United States Patent
Zalevsky

(10) Patent No.: US 7,365,917 B2
(45) Date of Patent: Apr. 29, 2008

(54) OPTICAL METHOD AND SYSTEM FOR EXTENDED DEPTH OF FOCUS

(75) Inventor: Zeev Zalevsky, Rosh HaAyin (IL)

(73) Assignee: Xceed Imaging Ltd., Rosh Haayin (IL)

( * ) Notice: Subject to any disclaimer, the term of this patent is extended or adjusted under 35 U.S.C. 154(b) by 0 days.

(21) Appl. No.: 11/707,271

(22) Filed: Feb. 16, 2007

(65) Prior Publication Data

US 2007/0236769 A1    Oct. 11, 2007

Related U.S. Application Data

(63) Continuation-in-part of application No. PCT/IL2005/000868, filed on Aug. 11, 2005, and a continuation-in-part of application No. 10/974,943, filed on Oct. 28, 2004, now Pat. No. 7,061,693.

(60) Provisional application No. 60/601,938, filed on Aug. 16, 2004.

(51) Int. Cl.
G02B 9/00 (2006.01)

(52) U.S. Cl. .................. 359/738; 359/739; 359/559

(58) Field of Classification Search ................ 359/738, 359/739, 559, 558, 721, 740; 438/468, 535, 438/508
See application file for complete search history.

(56) References Cited

U.S. PATENT DOCUMENTS

| 3,549,240 A | 12/1970 | Sawatari et al. |
| 4,955,904 A | 9/1990 | Atebara et al. |
| 5,225,858 A | 7/1993 | Portney |
| 5,245,367 A | 9/1993 | Miller et al. |
| 5,260,727 A | 11/1993 | Oksman et al. |
| 5,302,477 A | 4/1994 | Dao et al. |
| 5,662,706 A | 9/1997 | Legerton et al. |
| 5,715,031 A | 2/1998 | Roffman et al. |
| 5,748,371 A | 5/1998 | Cathey, Jr. et al. |
| 5,757,458 A | 5/1998 | Miller et al. |

(Continued)

FOREIGN PATENT DOCUMENTS

EP    0 369 561    5/1990

(Continued)

OTHER PUBLICATIONS

Bradburn S. et al.: "Realization of focus invariance in optical-digital systems with wave-front coding"; *Applied Optics, OSA, Optical Society of America*, vol. 36, No. 35, 1997, pp. 9157-9166.

(Continued)

*Primary Examiner*—Timothy Thompson
(74) *Attorney, Agent, or Firm*—Browdy and Neimark

(57) ABSTRACT

An imaging arrangement and method for extended the depth of focus are provided. The imaging arrangement comprises an imaging lens having a certain affective aperture, and an optical element associated with said imaging lens. The optical element is configured as a phase-affecting, non-diffractive optical element defining a spatially low frequency phase transition. The optical element and the imaging lens define a predetermined pattern formed by spaced-apart substantially optically transparent features of different optical properties. Position of at least one phase transition region of the optical element within the imaging lens plane is determined by at least a dimension of said affective aperture.

46 Claims, 13 Drawing Sheets

U.S. PATENT DOCUMENTS

| | | |
|---|---|---|
| 5,768,031 A | 6/1998 | Yang |
| 5,786,883 A | 7/1998 | Miller et al. |
| 5,905,561 A | 5/1999 | Lee et al. |
| 5,965,330 A | 10/1999 | Evans et al. |
| 5,980,040 A | 11/1999 | Xu et al. |
| 6,024,447 A | 2/2000 | Portney |
| 6,069,738 A | 5/2000 | Cathey, Jr. et al. |
| 6,097,856 A | 8/2000 | Hammond, Jr. |
| 6,172,957 B1 | 1/2001 | Ogasawara |
| 6,451,056 B1 | 9/2002 | Cumming et al. |
| 6,474,814 B1 | 11/2002 | Griffin |
| 6,527,389 B2 | 3/2003 | Portney |
| 6,533,416 B1 | 3/2003 | Fermigier et al. |
| 6,537,317 B1 | 3/2003 | Steinert et al. |
| 6,554,424 B1 | 4/2003 | Miller et al. |
| 6,554,859 B1 | 4/2003 | Lang et al. |
| 6,576,012 B2 | 6/2003 | Lang |
| 7,061,693 B2 | 6/2006 | Zalevsky |
| 2003/0142268 A1 | 7/2003 | Miller et al. |
| 2004/0114102 A1 | 6/2004 | Miller et al. |
| 2004/0114103 A1 | 6/2004 | Miller et al. |
| 2004/0145808 A1 | 7/2004 | Cathey et al. |
| 2004/0230299 A1 | 11/2004 | Simpson et al. |

FOREIGN PATENT DOCUMENTS

| | | |
|---|---|---|
| WO | WO 99/57599 | 11/1999 |
| WO | WO 01/35880 | 5/2001 |
| WO | WO 03/012528 | 2/2003 |
| WO | WO 03/032825 | 4/2003 |
| WO | WO 03/052492 | 6/2003 |
| WO | WO 03/076984 | 9/2003 |

OTHER PUBLICATIONS

Fitzgerrell, A.R. et al., "Defocus Transfer Function For Circularly Symmetric Pupils"; *Applied Optics Opt. Soc. America, U.S.A.*, vol. 36, No. 23, 1997, pp. 5796-5804.

Varant C. et al.; Imaging properties of defocused partioned pupils; *Journal of Society of America, Optics and Image Science*, vol. 2, No. 6, 1985, pp. 799-802.

Luis Alberto Carvalho, "A Simple mathematical model for simulation of the human optical system based on in vivo corneal data", Revista Brasileira de Engenharia Biomedica, vol. 19, No. 1, pp. 29-37, Apr. 2003.

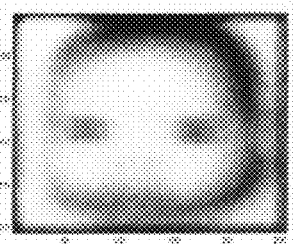
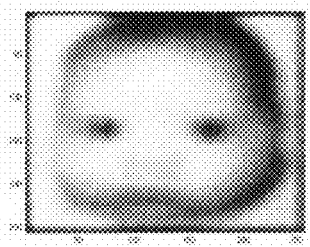
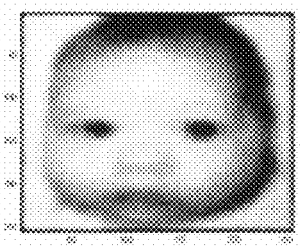
FIG. 5A   FIG. 5B   FIG. 5C
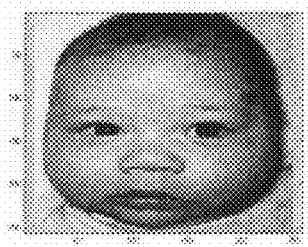
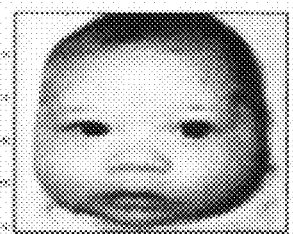
FIG. 5D   FIG. 5E   FIG. 5F
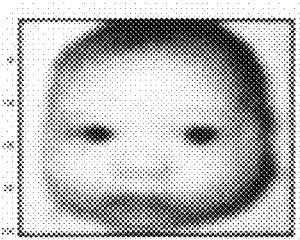
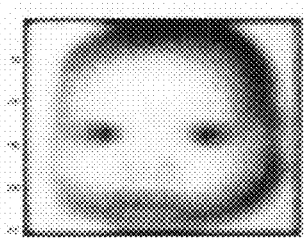
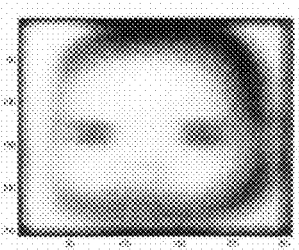
FIG. 5G   FIG. 5H   FIG. 5I
FIG. 6

OPTICAL METHOD AND SYSTEM FOR EXTENDED DEPTH OF FOCUS

FIELD OF THE INVENTION

This invention is generally in the field of imaging systems, and relates to an imaging lens arrangement with increased depth of focus.

BACKGROUND OF THE INVENTION

Extending the depth of focus of imaging systems is a very important core technology allowing its incorporation into various applications, including inter alia medically related applications where elements, such as cameras, are to be inserted into the body in order to observe and detect problematic tissues; as well as ophthalmic industry including glasses for spectacles, contact lenses, intraocular lenses or other lenses inserted surgically into the eye. The extended depth of focus solution is also needed for optical devices like microscopes or cameras for industrial, medical, surveillance or consumer applications, where focusing of light is required and where today focusing is being implemented by a multitude of lenses with the need of relative displacement between the focusing arrangement and an image and/or object plane, by mechanical movement, either manually or electronically driven.

Various approaches have been developed for obtaining extended depth of focus of an optical system. One of the known approaches, developed by the inventor of the present invention, is disclosed in WO 03/076984. This technique provides an all-optical extended depth of field imaging. An imaging system produces images of acceptable quality of objects which are located at a wide variety of distances from the imaging system. A preferred embodiment of the imaging system includes an object, an auxiliary lens, a composite phase mask and a sensor arranged along an optical axis. Light from the object is focused by the auxiliary lens in tandem with the composite phase mask, producing an image which is incident on the detector. This technique is based upon placing a spatially highly resolved phase element on top of the lens aperture such that continuous set of focal length is generated.

Another approach is disclosed for example in the following publications: U.S. Pat. No. 6,069,738; U.S. Pat. No. 6,097,856; WO 99/57599; WO 03/052492. According to this approach, a cubic phase mask is used in the aperture plane, and digital post processing is required to realize a focused image. More specifically:

U.S. Pat. No. 6,069,738 discloses an apparatus and methods for extending depth of field in image projection systems. An optical system for providing an in-focus, extended depth of field image on a projection surface includes an encoded mask or light encoder for preceding the light to include object information (or, equivalently, information about the desired image), and an extended depth of field (EDF) mask, for extending the depth of field of the projection system. In addition to including object information, the encoded mask encodes the light from the light source to account for the variations introduced by the EDF mask in extending the depth of field, so that no post processing is required.

U.S. Pat. No. 6,097,856 discloses an apparatus and method for reducing imaging errors in imaging systems having an extended depth of field. An improved optoelectronic imaging system is adapted for use with incoherently illuminated objects, and which produces final images having reduced imaging error content. The imaging system includes an optical assembly for forming an intermediate image of the object to be imaged, an image sensor for receiving the intermediate image and producing an intermediate image signal, and processing means for processing the intermediate image signal to produce a final image signal having a reduced imaging error content. A reduction in imaging error content is achieved, in part, by including in the optical assembly a phase mask for causing the OTF of the optical assembly to be relatively invariant over a range of working distances, and an amplitude mask having a transmittance that decreases continuously as a function of distance from the center thereof. The reduction in imaging error content is also achieved, in part, by including in the processing means an improved generalized recovery function that varies in accordance with at least the non-ideal calculated IOTF of the optical assembly under a condition of approximately optimum focus.

WO 99/57599 discloses an optical system for increasing the depth of field and decreasing the wavelength sensitivity of an incoherent optical system. The system incorporates a special purpose optical mask into the incoherent system. The optical mask has been designed to cause the optical transfer function to remain essentially constant within some range from the in-focus position. Signal processing of the resulting intermediate image undoes the optical transfer modifying effects of the mask, resulting in an in-focus image over an increased depth of field. Generally the mask is placed at or near an aperture stop or image of the aperture stop of the optical system. Preferably, the mask modifies only phase and not amplitude of light, though amplitude may be changed by associated filters or the like. The mask may be used to increase the useful range of passive ranging systems.

WO 03/052492 discloses a technique providing extended depth of focus (EDF) to human eyes by modifying contact lenses, intraocular implants, or the surface of the eye itself. This is accomplished by applying selected phase variations to the optical element in question (for example, by varying surface thickness). The phase variations EDF-code the wavefront and cause the optical transfer function to remain essentially constant within some range away from the in-focus position. This provides a coded image on the retina. The human brain decodes this coded image, resulting in an in-focus image over an increased depth of focus.

Yet other approaches, disclosed for example in U.S. Pat. No. 6,554,424 (as well as U.S. patent application publications 20040114103; 20040114102; and 20030142268) and U.S. Pat. No. 4,955,904, utilize apodization of the aperture plane. More specifically:

U.S. Pat. No. 6,554,424 describes a system and method for increasing the depth of focus of the human eye. The system is comprised of a lens body, an optic in the lens body configured to produce light interference, and a pinhole-like optical aperture substantially in the center of the optic. The optic may be configured to produce light scattering or composed of a light reflective material. Alternatively, the optic may increase the depth of focus via a combination of light interference, light scattering, light reflection and/or light absorption. The optic may also be configured as a series of concentric circles, a weave, a pattern of particles, or a pattern of curvatures. One method involves screening a patient for an ophthalmic lens using a pinhole screening device in the lens to increase the patient's depth of focus. Another method comprises surgically implanting a mask in the patient's eye to increase the depth of focus.

U.S. Pat. No. 4,955,904 describes a masked intraocular lens for implantation into a human eye. The mask, which blocks only part of the lens body, together with the pupil of the eye, defines a small aperture in the eye when the pupil is constricted, thereby increasing the depth of focus, as a pinhole camera does. When the pupil of the eye is dilated, additional light is allowed to pass through the pupil around the mask and to reach the retina to allow a person to see in dimmer light conditions. In one embodiment, the mask defines a small circular aperture and a larger exterior annulus; the small circular aperture has an additional power intermediate between that needed for distance and close vision. Also provided is a method for treating a patient with cataracts comprising replacing the patient's lens with this masked intraocular lens.

Some other vision improvement techniques are disclosed in the following patent publications:

U.S. Pat. No. 5,748,371 discloses extended depth of field optical systems. The system for increasing the depth of field and decreasing the wavelength sensitivity and the effects of misfocus-producing aberrations of the lens of an incoherent optical system incorporates a special purpose optical mask into the incoherent system. The optical mask has been designed to cause the optical transfer function to remain essentially constant within some range from the in-focus position. Signal processing of the resulting intermediate image undoes the optical transfer modifying effects of the mask, resulting in an in-focus image over an increased depth of field. Generally the mask is placed at a principal plane or the image of a principal plane of the optical system. Preferably, the mask modifies only phase and not amplitude of light. The mask may be used to increase the useful range of passive ranging systems.

WO 01/35880 discloses multifocal aspheric lens, an optical surface in close proximity to a person's pupil for correcting presbyopia, a method for obtaining that optical surface, and a laser surgery system to carry out the method. The optical surface includes a first vision area, a second vision area surrounding the first area, and a third vision area surrounding the second vision area, the first vision area having a first substantially single power, the second vision area having a range of powers, the third vision area having a second substantially single power distinct from the first single power, at least one of the first, second and third vision areas having an aspheric surface, and the other areas having spherical surfaces. The method includes reshaping the cornea to obtain this optical surface. The cornea may be reshaped on the anterior or an underlying surface by ablation or collagen shrinkage, wherein the ablation is performed by applying an excimer laser, surgical laser, water cutting, fluid cutting, liquid cutting or gas cutting technique. The method also includes obtaining this optical surface by placing a contact lens having the desired optical characteristics on the cornea. The laser surgery system includes a laser beam generator and a laser beam controller to regulate the beam striking the cornea to remove a selected volume of corneal tissue from a region in an optical zone of the cornea with the ablative radiation, thereby forming a reprofiled region which has a first vision area, a second vision area surrounding the first area, and a third vision area surrounding the second vision area.

U.S. Pat. No. 5,965,330 discloses methods for fabricating annular mask lens having diffraction-reducing edges. According to this technique, the lens body has an annular mask that forms a "soft edge" by gradually decreasing the transmissivity radially from the center aperture to the annular mask area. The methods introduce varying levels of a coloring agent (e.g., dye) into certain portions of the lens.

WO 03/012528 describes an apparatus for generating a light beam with an extended depth of focus. The apparatus includes a binary phase mask that generates a diffraction pattern including bright main ring and two side-lobe rings, an annular aperture mask that passes only part of the diffraction pattern, and a lens that causes the light passing through the annular aperture to converge towards and cross the optical axis. Where the converging light crosses the optical axis, constructive interference takes place, generating a light beam that has an extended depth of focus.

U.S. Pat. Nos. 5,786,883; 5,245,367 and 5,757,458 describe an annular mask contact lens designed to operate with the normal functioning of the human pupil. An annular mask forms a small pinhole-like aperture on the contact lens enabling continual focus correction. The outer diameter of the annular mask allows the wearer to transmit more light energy through the pupil as brightness levels decrease. The contact lens may be structured with two separate and distinct optical corrections, both at the small aperture region and in the region beyond the annular mask. Functional imaging is thus achieved for both bright and dim lighting, and over a wide range of viewing distances.

U.S. Pat. No. 5,260,727 discloses wide depth of focus intraocular and contact lenses. According to this technique, the lens power can be a constant but the amplitude and phase of the wave across the pupillary aperture are variables. The lens can be constructed by shading regions thereof in accordance with a mathematical function, e.g., a Gaussian distribution or Bessel function over a predetermined geometry, such as e.g., concentric, parallel or radial. The lens may be of single power or multiple power, e.g., of the bi-focal type.

U.S. Pat. No. 5,905,561 discloses an annular mask lens for vision correction having diffraction reducing edges. The lens body has an annular mask that forms a "soft edge" by gradually decreasing the transmissivity radially from the center aperture to the annular mask area.

U.S. Pat. No. 5,980,040 describes a pinhole lens and contact lens. The contact lens comprises an optically transparent lens body having a concave surface adapted to the patient's eye curvature and a convex surface. The lens has three regions: (1) an annular region of a first optical power; (2) at the center of said annular region, which is also at the optical center of said lens, a substantially pinhole-like aperture; and (3) a second larger annular region exterior to the first annular region.

U.S. Pat. No. 5,662,706 discloses a variable transmissivity annular mask lens for the treatment of optical aberrations, such as night myopia, spherical aberration, aniridia, keratoconus, corneal scarring, penetrating keratoplasty, and post refractive surgery complication. The lens has an annular mask having an aperture larger than conventional pinhole contact lens. The aperture having a "soft" inside edge and which mask has a gradually increasing transmissivity radially toward the outer edge of the mask.

U.S. Pat. No. 5,225,858 describes a multifocal ophthalmic lens adapted for implantation in the eye or to be disposed on or in the cornea. The lens has an optical axis, a central zone and a plurality of annular zones circumscribing the central zone. Two of the annular zones have a first region with a far vision correction power and a second region with a near vision correction power. In an IOL embodiment, the vision correction power between far and near is progressive, and each of the second regions has a major segment in which the near vision correction power is substantially constant. The power in the central zone varies.

U.S. Pat. No. 6,554,859 discloses an intraocular lens for implantation in an eye of a patient. The lens includes a multifocal optic and a movement assembly. The optic has maximum add power which is less than the add power required for full near vision for a pseudophakic eye. The movement assembly is coupled to the optic and is adapted to cooperate with the eye of the patient to effect accommodating movement of the optic in the eye. Lens systems including two optics and two movement assemblies are also provided. The intraocular lenses and lens systems are particularly useful when implanted in the eyes of a patient after removal of the natural lenses.

U.S. Pat. Nos. 6,576,012 and 6,537,317 disclose a binocular lens system for improving the vision of a patient. The system includes first and second ophthalmic lenses. Each of these lenses is adapted for implantation in an eye or to be disposed on or in the cornea. The first lens has a first baseline diopter power for distance vision correction and the second ophthalmic lens has a second baseline diopter power for other than distance vision correction. The ophthalmic lenses may be intraocular lenses which are implanted in the eyes of a patient or has natural lenses or following removal of the natural lenses.

U.S. Pat. No. 6,474,814 discloses a multifocal ophthalmic lens with induced aperture. The multifocal lenses are defined by nonconical aspheric optical surfaces. Various alternative surface shapes provide a central distance vision region surrounded by an optical step. The optical step has rapidly increasing power in the radial direction which creates an induced aperture through which the cortical elements of the vision system are induced to concentrate. The induced aperture results in increased clarity in distance vision. Nonconical aspheric optical surfaces are defined to produce the desired optical power distributions. These surface functions are also provided in form of polynomial series for simplicity of use in computer driven lathes for shaping contact lenses. This technique refers to contact lenses, scleral lenses, intraocular lenses, and lenses impressed or surgically shaped within the corneal tissue.

U.S. Pat. No. 6,527,389 describes an improved multifocal ophthalmic lens, which has a plurality of alternating power zones with a continuously varying power within each zone, as well as in transition from one zone to another. In other words, a plurality of concentric zones (at least two) are provided in which the variation from far to near vision correction is continuous, i.e., from near correction focal power to far correction focal power, then back to near, and again back to far, or vice versa. This change is continuous (progressive), without any abrupt correction changes, or "edges". Two versions of this technique are disclosed. In the first version continuous, alternating power variation is accomplished by a continuously changing curvature of the lens posterior surface, thereby altering the angle of impact of light rays on the eye. In the second version continuous, alternating power variation is accomplished by creating non-homogeneous surface characteristics having refractive material indexes which continuously vary in the lens radial direction (out from the optical axis).

U.S. Pat. No. 5,715,031 discloses concentric aspheric multifocal lens designs which use a combination of an aspheric front surface, which results in aberration reduction and contrast vision enhancement, along with a concentric multifocal back surface, to produce a lens design which affords clear vision at a distance and also near without a loss in contrast which is generally typical of prior art simultaneous vision, concentric multifocal lens designs. The aspheric surface improves the modulation transfer function (MTF) of the lens eye combination which improves the focus and contrast of both distance and near images. The design form is valid for contact lenses and intraocular lenses.

U.S. Pat. No. 6,024,447 discloses an enhanced monofocal ophthalmic lens for providing a monofocal vision correction power with an enhanced depth of focus. The lens is adapted to be implanted into an eye, placed over the eye, or to be disposed in a cornea of the eye. The ophthalmic lens includes a baseline diopter power for far vision correction, a first zone having a first vision correction power, and a second zone having a second vision correction power. The second zone is located radially outwardly of the first zone. The first zone includes a near vision correction power, and the second zone includes a far vision correction power. A maximum diopter value of the first zone is approximately 0.7 diopters above the baseline diopter, and a minimum diopter value of the second zone is approximately 0.5 diopters below the baseline diopter power. The first zone is adapted for focusing light at a first predetermined distance from the retina of the user, and the second zone is adapted for focusing light at a second predetermined distance from the retina of the user. The second predetermined distance is approximately opposite and equal to the first predetermined distance. A third zone, which is substantially similar to the first zone, is located radially outwardly of the second zone, and a fourth zone, which is substantially similar to the second zone, is located radially outwardly of the third zone. A third vision correction power of the third zone is approximately the same as the first vision correction power of the first zone, and a fourth vision correction power of the fourth zone is approximately the same as the second vision correction power of the second zone.

U.S. Pat. No. 6,451,056 describes an intraocular lens for increased depth of focus. The intraocular lens provides substantially increased depth of focus for accurate near and far vision with an optic much thinner than a natural lens, the lens being rigid, vaulted posteriorly and adapted for posterior positioning in the capsular bag. The optic is positioned substantially farther from the cornea than a natural lens, so that a cone of light exiting the optic to impinge upon the retina is much smaller than a cone of light from a natural lens. Typically, the optic may be about 1.0 mm thick and its distance from the cornea 7.0-8.0 mm.

WO 03/032825 discloses a method of designing a contact lens or other correction for providing presbyopia correction to a patient. The method relies on wavefront aberration measurement data for providing a best form correction. Preferably the correction is in the form of a multifocal translating style alternating vision contact lens or a simultaneous vision style correcting lens. A method for designing a correction for improving a person's vision is directed to correcting higher order aberrations in such a manner that a residual amount of the higher-order rotationally symmetric aberration is greater than a residual amount of the higher-order rotationally asymmetric aberration after the correction. The design method is directed to correcting asymmetric higher order aberrations induced by decentering of a multifocal contact lens that has residual spherical aberration which provides increased depth of field.

EP 0369561 discloses a system and process for making diffractive contact and intra-ocular lenses. The optical system includes the following principal elements in optical alignment along an optical axis, for accomplishing the indicated steps of the process: a laser for emission of ultraviolet light along the optical axis; a zone plate mask in the path of irradiation by the laser; and an imaging lens to project, with radiation from the laser, an image of the mask on the concave inner surface of an eye lens mounted coincident with the image surface of the optical system, thereby ablating the eye lens imagewise of the mask to generate a phase zone plate on the eye lens. The laser beam scans the zone plate mask to generate a composite image on the image surface. Alternatively, the phase zone plate is generated on the concave surface of a glass blank at the image surface to form a tool from which molds, and in turn lenses, are replicated. The light source is an argon fluoride excimer laser, emitting at 193 nm. The lens is a variable magnification lens to project various size images of the mask for producing zone plates of various powers as desired.

The known techniques, however, suffer from such drawbacks as unavoidable scattering of a significant part of energy towards the outer regions of a field of view of the system; the need for digital post processing; damaging the spatial frequencies transmission and the energetic efficiency.

SUMMARY OF THE INVENTION

There is accordingly a need in the art for an all-optical extended depth of focus technique.

The present invention solves the above problems by providing an imaging arrangement utilizing an optical element located adjacent to, attached to the surface of, or incorporated within an effective aperture of the imaging arrangement. It should be noted that the term "effective aperture of the imaging arrangement" used herein signifies a light collecting aperture, which may be the actual size of an imaging lens itself or an aperture in front of the imaging lens, as the case may be, for example the eye's pupil in ophthalmic applications. It should also be noted that the imaging arrangement of the present invention may utilize a an array of lenses (lenslet array), in which case an array of optical elements is used, each optical element being associated with a corresponding one of the lenses.

The optical element of the present invention is configured as a phase-affecting, non-diffractive, thin-layer optical element that codes the lens aperture so as to provide an all-optical effect of extending the depth of focus. The optical element may be configured as a phase-only element or as a phase and amplitude affecting element. The term "all-optical" used herein signifies that a need for image processing is eliminated or at least substantially reduced.

The optical element is thus insensitive to wavelength and polychromatic illumination, does not scatter energy towards the outer regions of the field of view thus providing a very high energetic efficiency at the region of interest (close to 100%), and does not require apodization. It is important to note that such a high efficiency cannot be achieved by a diffractive optical element even if it is phase-only element, because of the divergence of light to unwanted diffraction orders. Since the technique of the present invention does not require digital post processing, it is adequate for ophthalmic applications or other "non-computer" based applications.

The optical element of the present invention is configured to define a mask (preferably a binary mask) of spatially low frequencies transitions. This may actually be achieved by designing the optical element so as to define at least one transition region (e.g., line or circle), to be surrounded by regions of the imaging lens, in the plane of the imaging lens. This at least one region of the optical element together with the imaging lens' regions define a predetermined pattern formed by spaced-apart optically transparent features of different optical properties (i.e., differently affecting the phase of light passing through the imaging lens arrangement).

The position(s) of the transition region(s) of the optical element within the imaging lens plane (i.e., the affective aperture plane) are selected, considering at least the affective aperture size of the imaging lens. These positions are appropriately selected so as to generate proper phase interference relation between light portions passing through different regions of the lens arrangement corresponding to the different features of the pattern, to thereby enable reducing a quadratic phase factor resulting from light getting out of focus of the imaging lens and thus maximize a defocused optical transfer function (OTF) of the imaging lens arrangement.

As indicated above, in order to design the optimal configuration for the extended depth of focus (EDOF) optical element, the effective aperture of the imaging lens is to be taken into consideration. The optical power distribution of the imaging lens and/or focal length may also be taken into consideration: since the EDOF has no optical power, it may be added to an imaging lens in order to shift the range of extended depth of focus around a certain given optical power.

The optimal geometry and dimensions of the EDOF element (i.e., at least one transition region) are determined using an optimization algorithm (based on a numerical or analytical approach, resulting in a spatially low frequency all-optical extended depth of focus), which determines N position(s) for the transition region(s) of the element within a given imaging lens (i.e., for a given effective aperture size).

Considering ophthalmic applications, where the effective aperture of the lens (eye pupil, or contact lens, or lens of spectacles) can be defined by a certain relatively narrow range of values common for most of patients, the EDOF of the present invention can be designed to be universal for a great amount of patients. Such a universal EDOF is configured to allow the depth of focus region equivalent to 5 diopters for the effective aperture of 2-3 mm. For a smaller percentage of patients having a higher difference between the near and far vision, the design of the EDOF element takes into account the optical power of the imaging lens with which the element is associated.

The position of the transition(s) (being pi-phase transition for a certain wavelength for which the EDOF is designed) generates invariance to quadratic phase distortions (which multiply the CTF of the imaging lens, corresponding to the effect of getting out of focus) under the operation of auto correlation. Due to the fact that the aperture mask (formed by the EDOF and imaging lens) is constructed out of spatially low-frequency transitions, it does not spread energies away from the zero order of diffraction and its energetic efficiency is close to 100%.

It should be noted that auto correlating the CTF is done to compute the optical transfer function (OTF) of the imaging system. The position of the EDOF transition(s) may be computed using iterative algorithm in which M positions are examined and eventually those of them are selected, which provide maximal contrast of the OTF under a set of out of focus locations. The meaning of OTF's contrast optimization (maximizing) is actually having the out of focused OTF bounded as much as possible away from zero.

The extended depth of focus (EDOF) element of the present invention is configured to generate proper phase interference relation allowing significant cancellation of the quadratic phase factor obtained due to getting out of focus. The EDOF element is a phase-affecting element (e.g., phase-only binary mask element), which is neither a refractive nor a diffractive element. In contrast to a refractive element, the EDOF filter of the present invention can be produced as a thin phase layer constructed in a low-cost lithographic technique or stamping with the thickness of the phase layer being of only one wavelength (e.g., around 0.5 micron in the case of ambient light illumination), similar to the fabrication approaches used for the conventional diffractive optical elements. On the other hand, in contrast to diffractive optical elements, the EDOF of the present invention has the spatial feature(s) of very low frequency. The element contains only very limited number of features and periods at low spatial frequency (period of about 1,000 wavelengths). The property of the optical element of the present invention allows for obtaining truly energetic efficient EDOF, since not only all the energy is passed through the element itself (it is substantially phase only) but also all of the energy is concentrated at the proper transversal and longitudinal region of interest (in contrast to a diffractive element that has energetic split either between multiple longitudinal focal planes or between traversal diffraction orders).

Hence, high energetic efficiency (close to 100%) of the optical element of the present invention provides extended depth of focus, in contrast to approaches based on the use of diffractive optical elements that split the energy between several diffraction orders/focal planes and that are basically equivalent to smaller lens aperture (also having larger depth of focus). In addition, the low spatial frequency of the invented approach eliminates its sensitivity to wavelength and polychromatic illumination which is a problematic topic with diffractive optical elements. Additionally, it is important to note that the invented approach is an all-optical technique that does not require numerical computation, and when it is used for ophthalmic applications it does not assume brain based decoding or adaptation process since an extended depth of focus image is identical to the image of an object itself.

There is thus provided according to one broad aspect of the present invention, an imaging arrangement comprising: an imaging lens assembly including at least one lens having a certain affective aperture, and at least one optical element associated with said at least one lens and configured to provide an extended depth of focus of the imaging arrangement, said optical element being configured as a phase-affecting, non-diffractive optical element defining a spatially low frequency phase transition, said optical element together with its associated lens defining a predetermined pattern formed by spaced-apart optically transparent features of different optical properties, position of at least one phase transition region of the optical element within the lens plane being determined by at least a dimension of said affective aperture.

According to another broad aspect of the invention, there is provided an imaging arrangement comprising: an imaging lens assembly including at least one lens having a certain affective aperture, and at least one optical element associated with said at least one lens and configured to provide an extended depth of focus of the imaging arrangement, said optical element being configured as a phase-only, non-diffractive binary mask defining a spatially low frequency phase transition, said optical element together with its associated lens defining a predetermined pattern formed by spaced-apart optically transparent features of different optical properties, position of at least one phase transition region of the optical element within the lens plane being determined by at least a dimension of said affective aperture.

According to yet another aspect of the invention, there is provided an imaging arrangement comprising: an imaging lens assembly including at least one lens having a certain affective aperture, and at least one optical element associated with said at least one lens and configured to provide an extended depth of focus of the imaging arrangement, said optical element being configured as a phase-affecting, non-diffractive optical element defining a spatially low frequency phase transition, said optical element together with its associated lens defining a predetermined pattern formed by spaced-apart optically transparent features of different optical properties, position of at least one phase transition region of the optical element within the lens plane being determined by at least a dimension of said affective aperture such that the optical element produces proper phase interference relation between light portions passing through different regions of the imaging arrangement corresponding to the different features of the pattern to thereby reduce a quadratic phase factor resulting from light getting out of focus of the imaging lens and maximize a defocused optical transfer function (OTF) of the imaging lens arrangement by providing the out of focus OTF as much as possible away from zero.

According to yet another broad aspect of the invention, there is provided an imaging arrangement comprising an imaging lens assembly including at least one lens having a certain affective aperture, and at least one optical element associated with said at least one imaging lens and configured to provide an extended depth of focus of the imaging arrangement, said optical element being configured as a phase-affecting, non-diffractive element defining a certain pattern of spatially low frequency phase transitions within a plane of the imaging lens, such that said optical element together with its associated imaging lens determine a predetermined pattern formed by spaced-apart optically transparent features differently affecting phase of light passing through the imaging arrangement, positions of the phase transitions of the optical element within the imaging lens plane being determined by at least a dimension of said affective aperture to reduce sensitivity of the imaging arrangement to shifts of a Coherent Transfer Function (CTF) of the imaging lens while getting out of focus.

According to yet another broad aspect of the invention, there is provided an imaging arrangement comprising an array of lenses each having a certain affective aperture, and an array of optical elements each optical element being associated with one lens of the lenslet array and being configured to provide an extended depth of focus of the imaging arrangement, said optical element being configured as a phase-affecting, non-diffractive optical element defining a spatially low frequency phase transition, said optical element together with its associated lens defining a predetermined pattern formed by spaced-apart optically transparent features of different optical properties, position of at least one phase transition region of the optical element within the lens plane being determined by at least a dimension of said affective aperture.

According to yet another aspect of the invention, there is provided an imaging lens for use in patients' spectacles, the imaging lens being configured to define a certain affective aperture and carrying an optical element configured to provide an extended depth of focus, said optical element being configured as a phase-affecting, non-diffractive optical element defining a spatially low frequency phase transition, said optical element together with its associated lens defining a predetermined pattern formed by spaced-apart optically transparent features of different optical properties, position of at least one phase transition region of the optical element within the lens plane being determined by at least a dimension of said affective aperture.

According to yet another aspect of the invention, there is provided a display device carrying an imaging arrangement, which comprises an array of imaging lenses each having a certain affective aperture, and an array of optical elements each associated with a corresponding one of said lenses and configured to provide an extended depth of focus, said optical element being configured as a phase-affecting, non-diffractive optical element defining a spatially low frequency phase transition, said optical element together with its associated lens defining a predetermined pattern formed by spaced-apart optically transparent features of different optical properties, position of at least one phase transition region of the optical element within the lens plane being determined by at least a dimension of said affective aperture.

It should be understood that such a display device may be a dynamic-type device for use with or being part of an electronic device (such as a mobile phone) or may be a static display device.

According to yet another aspect of the invention, there is provided a system for creating an image of an object on a detector plane, the system comprising an imaging lens arrangement formed by an imaging lens assembly including at least one lens having a certain affective aperture and at least one optical element configured to provide an extended depth of focus of the imaging arrangement, said optical element being configured as a phase-affecting, non-diffractive element defining a spatially low frequency phase transition, said optical element together with its associated imaging lens defining a predetermined pattern formed by spaced-apart optically transparent features of different optical properties, position of at least one phase transition region of the optical element within the imaging lens plane being determined by at least a dimension of said affective aperture such that the optical element produces proper phase interference relation between light portions passing through different regions of the imaging arrangement corresponding to the different features of the pattern to thereby enable reducing a quadratic phase factor resulting from light getting out of focus of the imaging lens and maximize a defocused optical transfer function (OTF) of the imaging arrangement.

According to yet another aspect of the invention, there is provided an optical element for use with an imaging lens for extending depth of focus of imaging, the optical element being configured as a phase-affecting, non-diffractive optical element defining a predetermined pattern of spatially low frequency phase transitions, said pattern being defined by an affective aperture of the given imaging lens.

According to yet another aspect of the invention, there is provided an optical element for use with an imaging lens for extending depth of focus of imaging, the optical element being configured as a phase-only, non-diffractive binary element defining a predetermined pattern of spatially low frequency phase transitions, said pattern being defined by an affective aperture of the given imaging lens. According to yet another aspect of the invention, there is provided an optical element for extending depth of focus of imaging, the optical element being configured as a phase-affecting, non-diffractive optical element defining a spatially low frequency phase transition.

According to yet another aspect of the invention, there is provided an optical element for extending depth of focus of imaging, the optical element being configured as a phase-affecting, non-diffractive optical element defining a spatially low frequency phase transition, the optical element defining a predetermined pattern of phase transition regions, said transition regions being arranged in accordance with an affective aperture of a given imaging lens for which the optical element is designed, so as to provide said transition regions of the optical element within predetermined positions in the imaging lens plane, to provide periodic replication of a lateral phase shape of a light field propagating through the imaging lens with said optical element.

According to yet another aspect of the invention, there is provided an optical element for extending depth of focus of imaging, the optical element being configured as a phase-only, non-diffractive binary element defining a spatially low frequency phase transition, the optical element defining a predetermined pattern of phase transition regions, said transition regions being arranged in accordance with an affective aperture of a given imaging lens for which the optical element is designed, so as to provide said transition regions of the optical element within predetermined positions in the imaging lens plane, to provide periodic replication of a lateral phase shape of a light field propagating through the imaging lens with said optical element.

According to yet another aspect of the invention, there is provided a method for providing a certain extended depth of focus of an imaging system, the method comprising applying an aperture coding to an imaging lens having a certain effective aperture, by applying to the imaging lens a phase-affecting non-diffractive optical element configured to define a spatially low frequency phase transition arrangement and thereby provide a predetermined pattern of spaced-apart substantially optically transparent features of different optical properties within the imaging lens plane, thereby producing phase interference relation between light portions passing through different regions of the lens arrangement corresponding to the different features of the pattern so as to reduce a quadratic phase factor resulting from light getting out of focus of the imaging lens and maximize a defocused optical transfer function (OTF) of the imaging lens arrangement.

According to yet another aspect of the invention, there is provided a method for providing a certain extended depth of focus of an imaging system, the method comprising designing a phase-affecting non-diffractive optical element to be used with an imaging lens having a certain effective aperture, said designing comprising selecting N positions for phase transitions within the imaging lens effective aperture as those providing maximal contrast of an Optical Transfer Function (OTF) of the imaging system under a set of out of focus locations, thereby providing the out of focus OTF as much as possible away from zero.

BRIEF DESCRIPTION OF THE DRAWINGS

In order to understand the invention and to see how it may be carried out in practice, preferred embodiments will now be described, by way of non-limiting example only, with reference to the accompanying drawings, in which:

FIGS. 5A to 5I exemplify face images obtained with the out of focus parameter $4\psi/D^2$ varying from −0.2 (FIG. 5A) up to 0.2 (FIG. 5I) at steps of 0.05, for the case where no optical element of the present invention is used;

FIG. 6 shows the results of examining the sensitivity of the optical element to wavelength variations;

FIG. 7A corresponding to the in focus position of Rosette with no EDOF element, FIG. 7B corresponds to in-focus position with the EDOF element, FIG. 7C corresponds to the out of focus position of Rosette with no EDOF element, and FIG. 7D corresponds to the out of focus position with the EDOF element;

DETAILED DESCRIPTION OF THE INVENTION

Figure 1A:
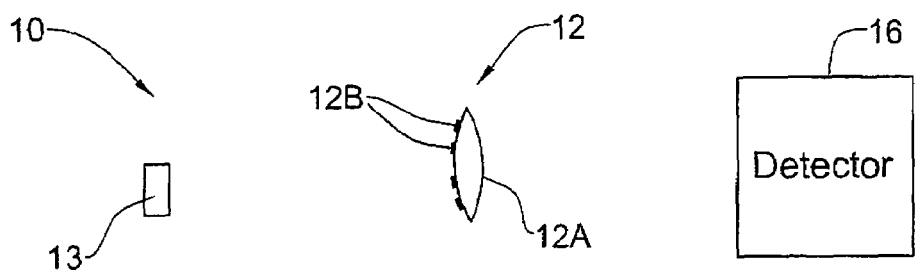
FIG. 1A is a schematic illustration of an example of an imaging system utilizing an imaging lens arrangement configured according to the present invention.

Referring to FIG. 1A, there is schematically illustrated an imaging system 10 utilizing an imaging lens arrangement 12 of the present invention. The imaging system 10 is formed by an object 13 that is to be imaged, the imaging lens arrangement 12, and a light detector unit 16. The imaging lens arrangement 12 includes a certain number of lenses 12A (generally at least one lens, single lens being shown in the present example) having a certain effective aperture D (which in the present example is the lens diameter), and a certain number of optical elements 12B (single element in the present example) associated with the lens(es) 12A. Such optical element 12B is configured and operable as an extended depth of focus (EDOF) element.

The optical element 12B is configured in accordance with the parameters of the lens 12A, i.e., its effective aperture and optionally also the optical power distribution and/or focal length. The optical element 12B is configured as a phase-affecting non-diffractive mask. Preferably, as shown in the present example, the mask 12B is implemented integral with the lens, namely as a pattern on the lens surface.

Figure 1B:
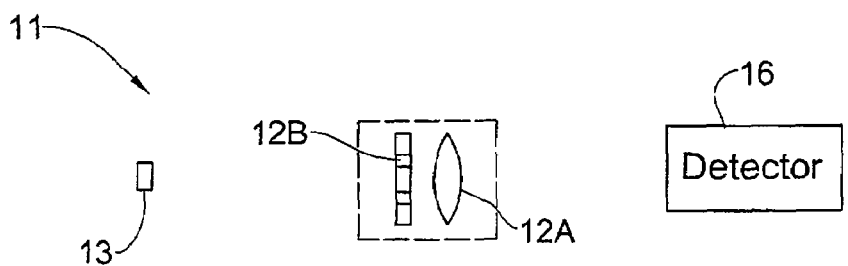
FIG. 1B schematically illustrates another example of an imaging lens arrangement of the present invention.

Generally, the mask 12B may be a separate element attached to the lens or located close thereto. This is illustrated in FIG. 1B showing an imaging system 100 utilizing a lens arrangement 112 that includes a lens 12A and a phase-affecting non-diffractive optical element 12B located close to the lens in front thereof.

Figure 1C:
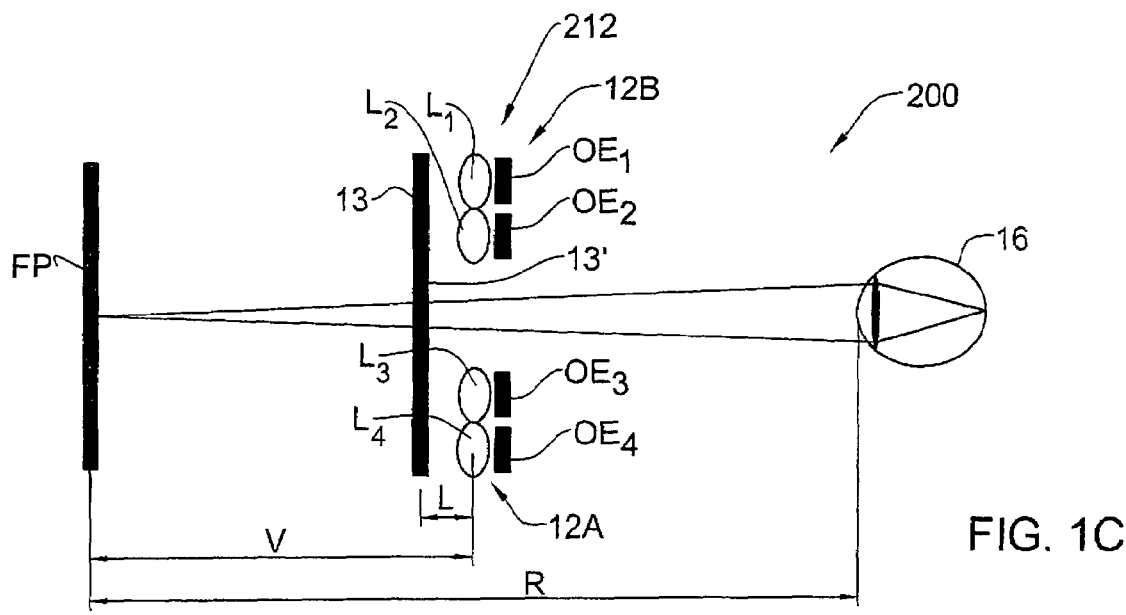
FIG. 1C schematically illustrates yet another example of an imaging lens arrangement of the present invention, suitable to be used with a display device.

FIG. 1C shows schematically an imaging system 200 according to yet another example of the invention. Here, an imaging lens arrangement 212 includes an array of lenses 12A, formed by four such lenses $L_1$, $L_2$, $L_3$ and $L_4$ in the present example, and an array 12B of optical elements $OE_1$, $OE_2$, $OE_3$ and $OE_4$ each associated with a corresponding lens of the lenslet array.

Such system 200 may for example be used with a display panel or screen 13 (constituting an object) aimed at facilitating the imaging of the display/screen (e.g., of a mobile phone device) by people having close vision problems. The imaging arrangement 212 is accommodated at a small distance (a few millimeters from a surface 13' of the display panel 13. Also, in the present example the optical elements' array 12B is located downstream of the lenslet array 12A with respect to light propagation from the object 13 towards a light detector 16 (patient's eye). The use of such lenslet' and EDOF elements' arrays provides for bringing the closest focus plane FP of the imaging arrangement 212 as close as possible to the object 13 plane, so that people with the close vision problems as well as people with normal vision will be able to see the screen. In addition, bringing the closest focus plane closer to the object plane reduces the demagnification ratio of the object that is to be focused.

Preferably, the optical element 12B is configured as a phase-only binary mask. It should, however be noted that generally the element 12B may be configured as a phase and amplitude mask.

The optical element 12B is configured to define at least one spatially low frequency transition region, and, together with the lens 12A regions, define a predetermined pattern of spaced-apart substantially optically transparent features differently affecting the phase of light passing therethrough. The pattern is thus formed by one or more transition regions of the optical element, spaced by the regions of the lens, in the imaging lens plane. The transition regions are pi-phase transitions for a certain wavelength for which the mask 12B is designed. The arrangement of these transition regions (positions within the lens 12A plane) is determined by the effective aperture of the given imaging lens 12A (and possibly also optical power of the lens) so as to maximize the defocused OTF of the entire imaging arrangement. To this end, the pattern is such as to generate proper phase interference relation between light portions passing through different regions of the lens arrangement to thereby enable reducing a quadratic phase factor resulting from light getting out of focus of the imaging lens.

Figure 1D:
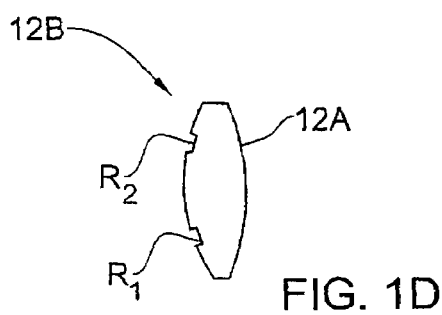
FIGS. 1D and 1E show two examples, respectively, of the optical element of the present invention being implemented integral with an imaging lens.
Figure 1E:
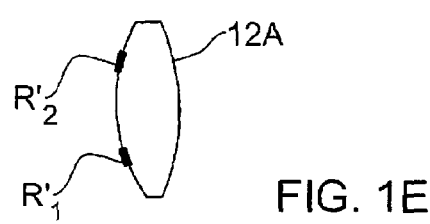

As shown in FIGS. 1D and 1E, the optical element may be implemented as a surface relief on the imaging lens (FIG. 1D), namely, a pattern of spaced-apart regions $R_1$ and $R_2$ of variable lens thickness; or as a pattern of lens regions $R'_1$ and $R'_2$ made of materials with different refractive indices $n_1$ and $n_2$ (FIG. 1E). In the case of different refractive index materials, a certain optically transparent material of a refractive index different from that of the lens may be coated on selective spaced-apart regions of the lens surface.

Figure 2A:
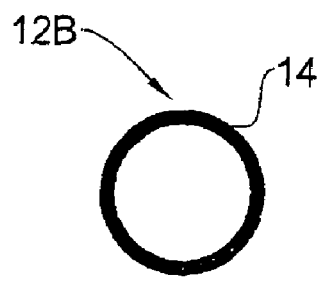
FIGS. 2A to 2C show three examples, respectively, of the contour of the optical element of the present invention suitable to be used in the imaging lens arrangement.
Figure 2B:
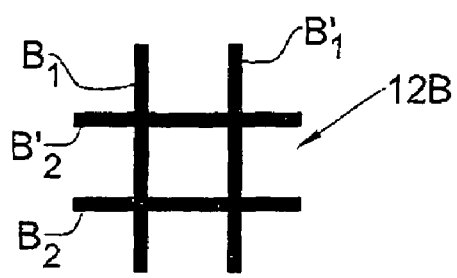
Figure 2C:
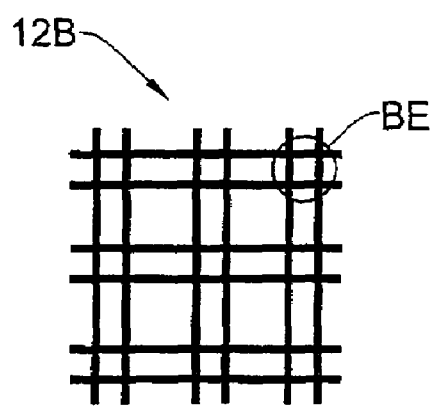
Figure 3A:
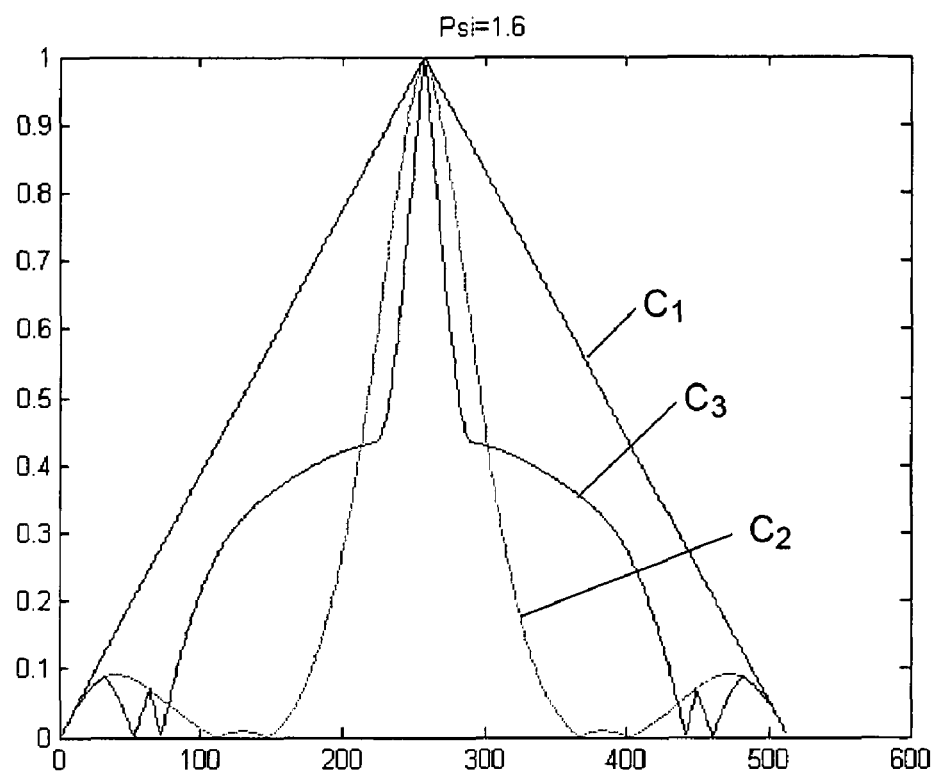
FIGS. 3A to 3D illustrate the effect of the present invention as compared to the conventional approach.
Figure 3B:
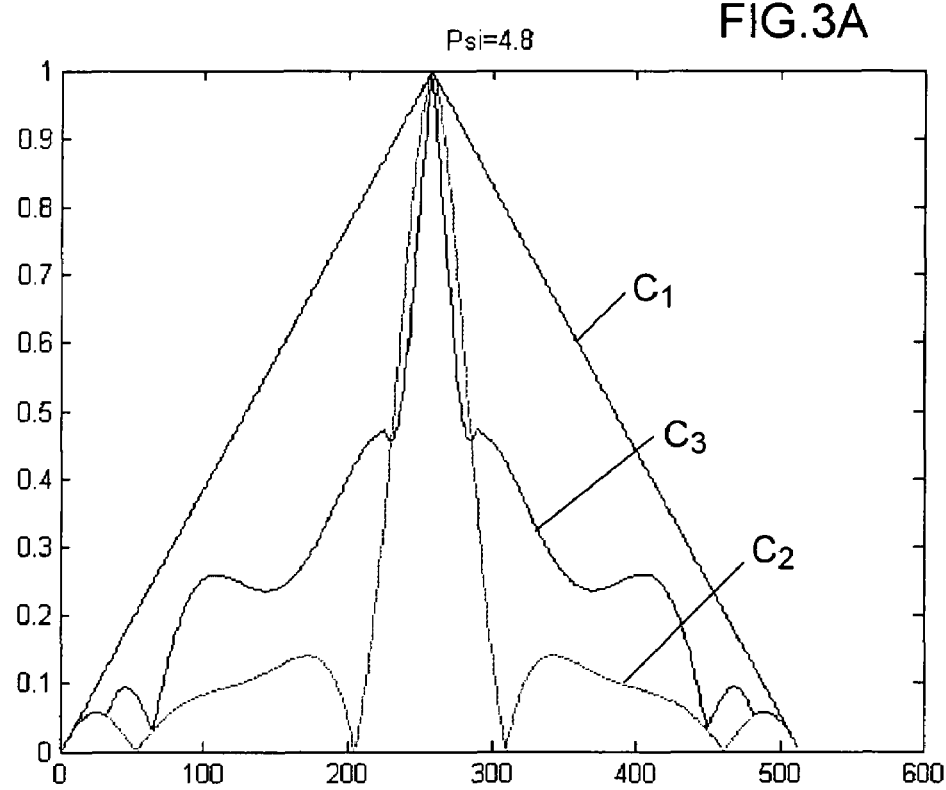
Figure 3C:
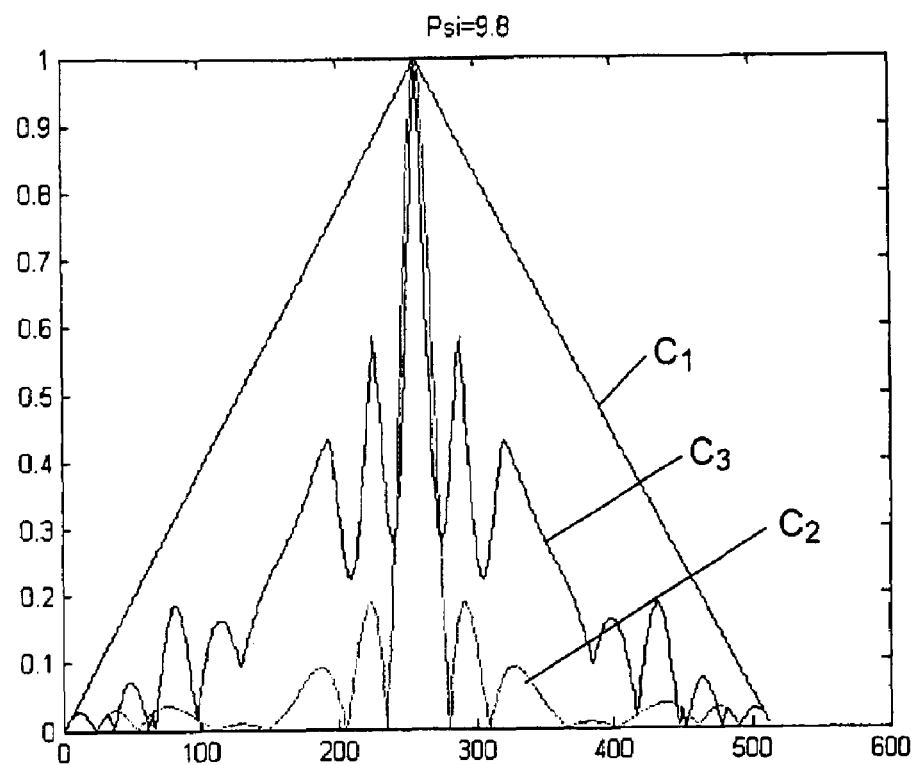
Figure 3D:
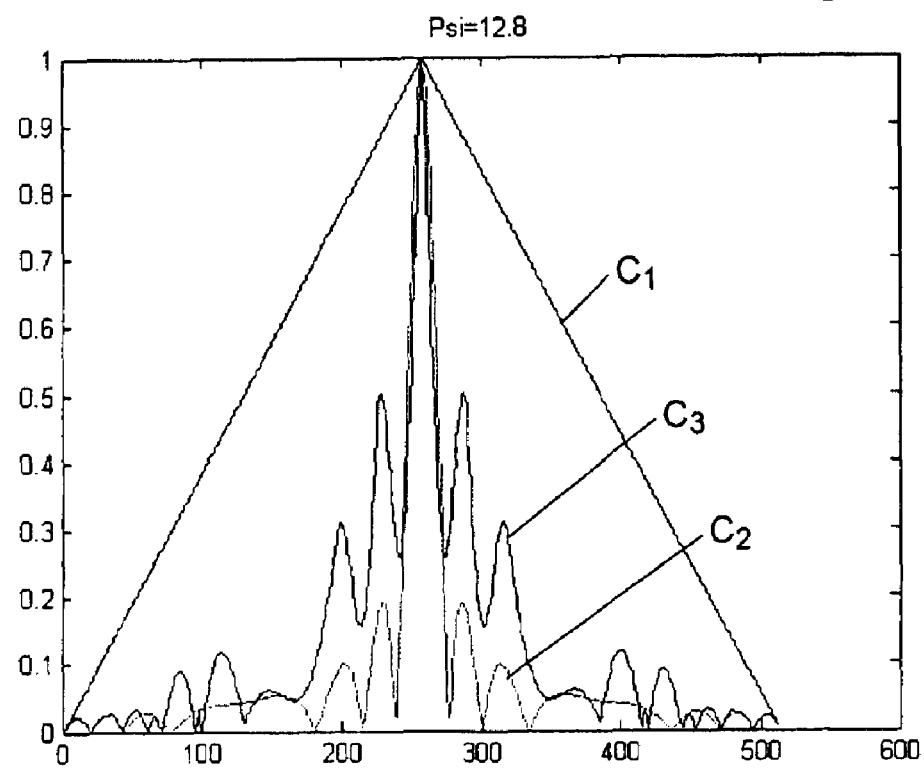
Figure 4A:
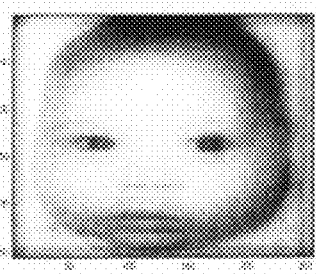
FIGS. 4A to 4I exemplify face images obtained with the out of focus parameter $4\psi/D^2$ varying from −0.2 (FIG. 4A) up to 0.2 (FIG. 4I) at steps of 0.05, for the case where the optical element of the present invention is used.
Figure 4B:
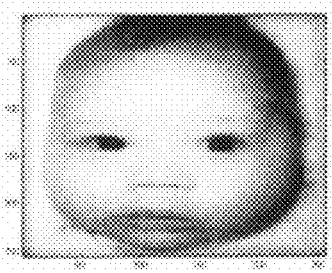
Figure 4C:
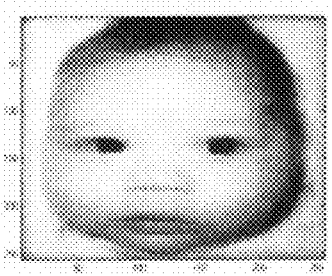
Figure 4D:
Figure 4E:
Figure 4F:
Figure 4G:
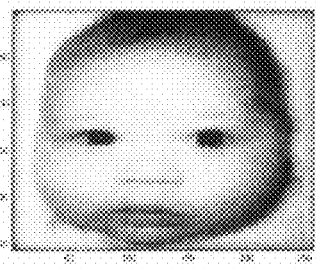
Figure 4H:
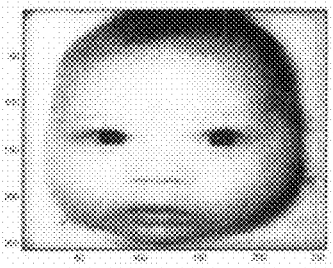
Figure 4I:
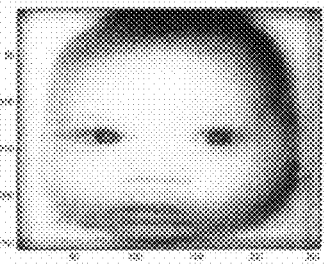

FIGS. 2A to 2C show two specific but not limiting examples, respectively, of the contour of the optical element 12B. In the example of FIG. 2A, the mask 12B is designed as an annular transition region 14 (generally, at least one such region; an array of concentric rings may be used as well). In the example of FIG. 2B the mask is designed as a grid formed by two mutually perpendicular pairs of bars (lines) $B_1$-$B'_1$ and $B_2$-$B'_2$. In the example of FIG. 2C, the element 12B is a mask formed by a two-dimensional array of basic grid-elements BE. For example, the transition regions along the bar line are pi-phase transitions and the regions of intersection between the perpendicular bars are zero-phase transitions. The optimized contour for the optical element is obtained solving an algorithm, which will be described further below.

It should be noted that the mask (pattern) may and may not be symmetrical relative to the center of the lens. In such an arrangement, for example, the four π-phase bars, two vertical (along Y-axis) and two horizontal (along X-axis) bars, that are illustrated in FIG. 2A, may be shifted transversally along the x-y plane to be not centered around the center of the lens.

It should also be noted, although not specifically shown, that the pattern may be configured to define microstructures inside the phase transition region (e.g., inside the pi-phase transition ring of FIG. 2A), namely, each phase transition region may be of a variable spatially low frequency of phase transition such as for example π/2, π, . . . .

The present invention provides the EDOF element 12B in the form of a mask of N segments within the effective aperture of the imaging lens 12A. It should be understood that instead of having a mask that blocks energy in some of segments and transmits in the other, the invention provides the substantially phase-only, non-diffractive mask 12B, that is either 1 or (−1) depending on the segment.

As indicated above, the mask 12B is designed to maximize the defocused OTF of the imaging system, by generating invariance to quadratic phase factor (which factor is generated when the image is defocused and multiplies the CTF of the imaging lens). To this end, in order to optimally design the mask 12B, a search is made for the segments that will obtain the transmission value of (−1) such that the OTF, due to the out of focus distortion, is bounded as much as possible away from zero. Since the mask 12B is a binary phase mask, no energy efficiency consideration is used (the transmission is 100%). Following these criteria, a search is made over all the possibilities and combinations for the aperture coding mask. The out of focus distortion is modeled by multiplying the aperture with the following expression:

$$\tilde{D}(v) = \exp\left(\frac{i4\Psi v^2}{D^2}\right) \quad (1)$$

wherein $\tilde{D}(v)$ is the CTF of the imaging lens 12A corresponding to the out of focus position of the object being imaged, D is the diameter of the imaging lens 12A (generally, the effective aperture of the lens), v is the coordinate of the aperture of the lens (in the plane of CTF), and ψ is the phase factor representing the amount of getting out of focus:

$$\Psi = \frac{\pi D^2}{4\lambda}\left(\frac{1}{u} + \frac{1}{v} - \frac{1}{F}\right) \quad (2)$$

wherein λ is the wavelength, u is the distance between the imaging lens 12A and the object 13, v is the distance between the imaging lens 12A and the sensor 16 (detector), and F is the focal length of the imaging lens. It should be noted that the term "imaging lens" refers here to the effective aperture thereof.

When imaging condition is fulfilled:

$$\frac{1}{u} + \frac{1}{v} = \frac{1}{F} \quad (3)$$

the distortion phase factor ψ equals zero.

The OTF is computed by auto-correlating the CTF with itself:

$$OTF(v) = CTF(v) \otimes CTF(v) \quad (4)$$

The auto correlation operation consists of shifting two CTF functions to the opposite directions, respectively, and then multiplying and summing the result. The so-obtained OTF relates to a spatial frequency that corresponds to the amount of the shift. At high frequencies (large shifts), the multiplication and the summing are averaged to zero in the case of out of focus. Hence, the OTF does not transmit high frequencies when the image is defocused.

The phase mask (e.g., ring) of the present invention is aimed at reducing the high-frequency cancellation at large shifts of the CTF (the OTF is an auto correlation of the CTF). To this end, the mask is configured to invert the sign of part of the light field that before (i.e., pure lens with no EDOF correction) was averaged to zero (and this is why the OTF did not transmit the high spatial frequencies).

The OTF is the Fourier transform of the intensity point spread function, and it is used to express the spatial-frequencies transmission function for intensity, when incoherent illumination is applied. Thus, the mathematical formulation for maximizing the OTF is as follows:

$$\max_{a_n}\left\{\min\left\{\left[\tilde{D}(v)\sum_{n=1}^{N}a_n rect\left(\frac{v - n\Delta v}{\Delta v}\right)\right] \otimes \left[\tilde{D}(v)\sum_{n=1}^{N}a_n rect\left(\frac{v - n\Delta v}{\Delta v}\right)\right]\right\}\right\} \quad (5)$$

i.e., find the values for $a_n$ that provide maximum for the minima of the auto correlation expression where $a_n=(1,-1)$ (it equals either 1 or −1).

It should be noted that the above-described iterative numerical algorithm is a specific but not limiting example of defining the EDOF element configuration. Other techniques can be used as well, for example numerical approached based on entropy minimization, or maximal likelihood, or other numerical or analytical approaches, resulting in a spatially low frequency all-optical extended depth of focus.

FIGS. 3A to 3D illustrate the effect of the present invention. Three examples of absolute value of the OTF (called Modulation Transfer Function—MTF) are obtained for different phase factor values: ψ=1.6 in FIG. 3A; ψ=4.8 in FIG. 3B; ψ=9.8 in FIG. 3C and ψ=12.8 in FIG. 3D. In each of these figures, curve $C_1$ corresponds to the MTF while at the in-focus state, curve $C_2$ corresponds to the defocused MTF of an imaging system without the use of the correction optical element (EDOF element) of the present invention (mask 12B in FIG. 1), and curve $C_3$ corresponds to the defocused MTF of the system with the correction element.

The transversal invariance may be obtained using the phase element producing periodic replication of the phase shape, namely lateral replication of the phase shape. Turning back to FIG. 2C exemplifying a mask formed by a two-dimensional array of basic elements BE, when large lateral shifts (high frequencies) exclude part of the phase shape, a complimentary part is inserted from another spatial period of the mask thus producing the phase period by replication. The replication of the basic period of the transitions (that of the basic element BE) thus reduces the sensitivity to lateral shifts. The longitudinal invariance is obtained as follows: Given the longitudinal distance between the phase element and a sensor (the imaging lens plane or the effective aperture plane), which is the lens of the human eye in case of ophthalmic applications, free space propagation of the mask function for this distance is considered. The result is a phase and amplitude distribution. The amplitude is dropped, leaving only the phase profile. In many cases, binarization of the phase function may provide sufficiently good results as well. The binarization realizes spatial mask which is easier for fabrication.

Reference is made to FIGS. 4A-4I and FIGS. 5A-5I illustrating how a face image looks like when the defocusing parameter $4\psi/D^2$ is varied from −0.2 (FIGS. 4A and 5A) up to 0.2 (FIGS. 4I and 5I) at steps of 0.05. FIGS. 4A-4I show the case where the mask (optimally designed) of the present invention is used, and FIGS. 5A-5I shows the case where no such aperture coding mask is used. In the present example, the EDOF element configured similar to that of FIG. 2B was used. As clearly seen in the figures, a difference in distortions between images of FIGS. 4A-4I and 5A-5I exists due to the aperture coding mask of the present invention.

FIG. 6 shows the results of examining the sensitivity of the coding mask (EDOF element) of the present invention to wavelength variations. In the present example, an imaging lens arrangement (imaging lens with a coding mask) was illuminated with wavelength $\lambda_1=0.8\lambda_0$, wherein $\lambda_0$ is the wavelength for which the mask was designed and fabricated to present pi-phase transition(s), and the defocusing parameter of $4\psi/D^2=0.15$ was used. As could be seen, the out of focus distortion obtained due to the usage of the mask is still very low despite the fact that the mask is no longer optimized (since the mask pattern features are pi-phase transitions for $\lambda_0$ and not for $\lambda_1$).

Figure 7A:
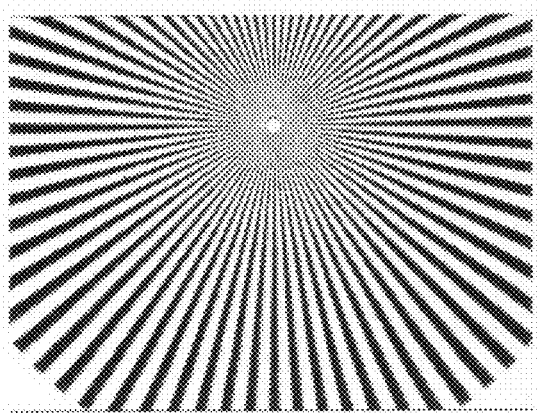
FIGS. 7A to 7D show experimental results for imaging a Rosette with and without the EDOF element of the invention.
Figure 7B:
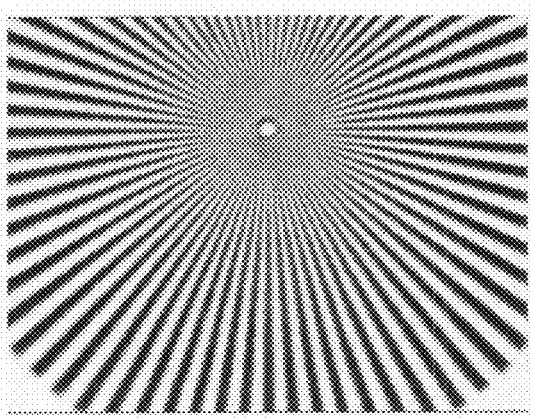
Figure 7C:
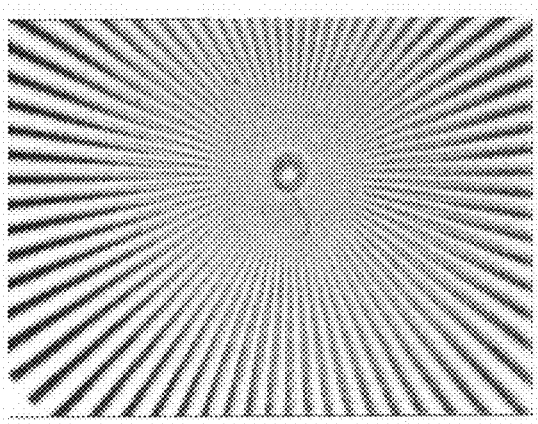
Figure 7D:
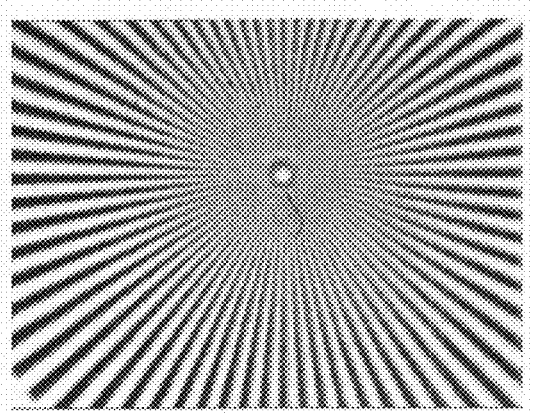

FIGS. 7A-7D show another experimental results obtained for imaging a Rosette. Here, FIG. 7A shows an image corresponding to the in focus position of the Rosette obtained with no EDOF element of the invention; FIG. 7B shows an in-focus image obtained with the EDOF element; FIG. 7C corresponds to the out of focus position of the Rosette with no EDOF element; and FIG. 7D shows an image of the out of focus Rosette obtained with the EDOF improvement of the present invention. In the present example, the EDOF element configured similar to that of FIG. 2A was used. As shown, the use of the EDOF element of the present invention provides improvement in spatial high frequencies and the effect on the input when the system is in focus.

It should be noted that in all the images presented in FIGS. 4A-4I, 5A-5I, 6 and 7A-7D, showing sufficient extension of the depth of focus, no digital post processing was applied. Applying such processing might further improve the obtained results.

The inventor has performed experimental verification of the extended depth of focus approach for polychromatic spatially non coherent illumination (general lighting). The experimental conditions were as follows: the focal length of the imaging lens F=90 mm, the distance between the imaging lens and the object v=215.9 mm, the distance between the imaging lens and detector (CCD) u=154.3 mm, the aperture of the imaging lens D=16 mm. Thus, the measurement for the phase distortion $\psi$ equals to 13 for the case where the object is moved a distance of 1.5 mm from the in cofus plane, and $\psi=17$ for moving the object a distance of 2 mm. The value of the phase factor $\psi$ is computed following equation 2 above and using the distances and the diameter of the lens (affective aperture of the lens) in the optical system. The experimental results under these conditions are shown in FIGS. 8A-8D and FIGS. 9A-9H. In the present example, the EDOF element configured similar to that of FIG. 2A was used.

Figure 8A:
FIGS. 8A to 8D and FIGS. 9A to 9H show experimental verification of the extended depth of focus technique of the present invention for polychromatic spatially non coherent illumination.
Figure 8B:
Figure 8C:
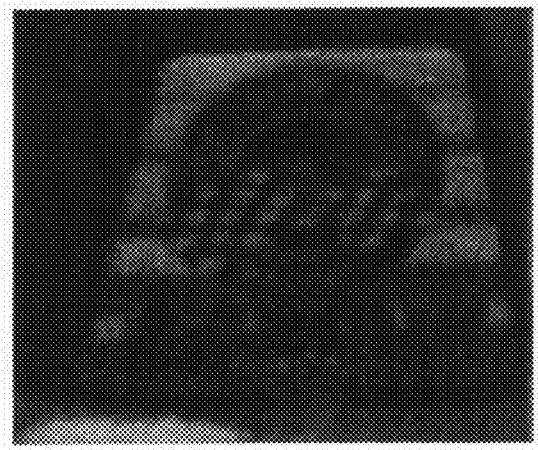
Figure 8D:
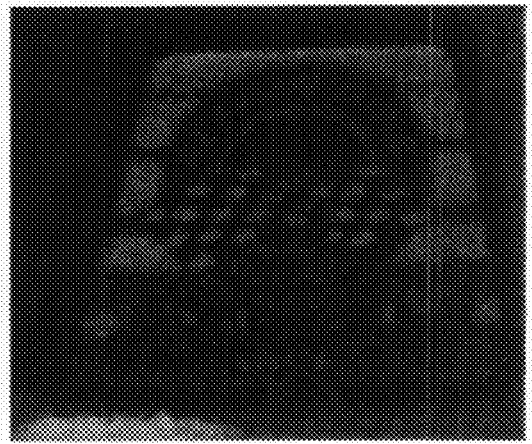

Here, FIG. 8A corresponds to an in-focus position without the use of the optical element of the present invention; FIG. 8B corresponds to the in-focus with such element, FIG. 8C corresponds to the defocused position without the optical element at $\psi=13$ (+1.5 mm), and FIG. 8D corresponds to the defocused position with the optical element at $\psi=13$ (+1.5 mm).

Figure 9A:
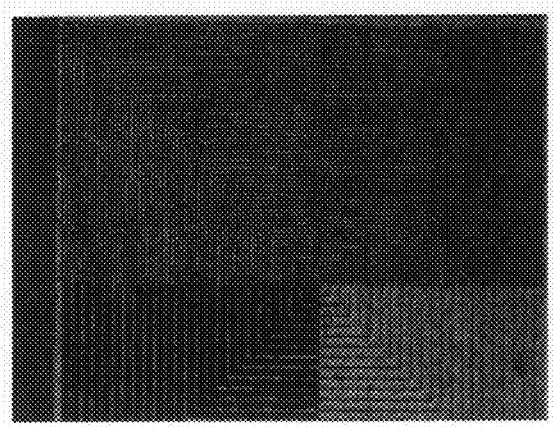
Figure 9B:
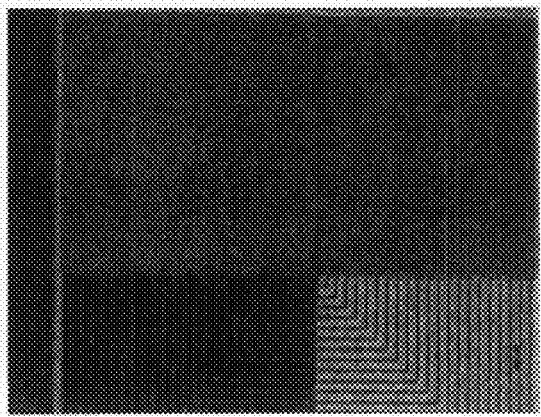
Figure 9C:
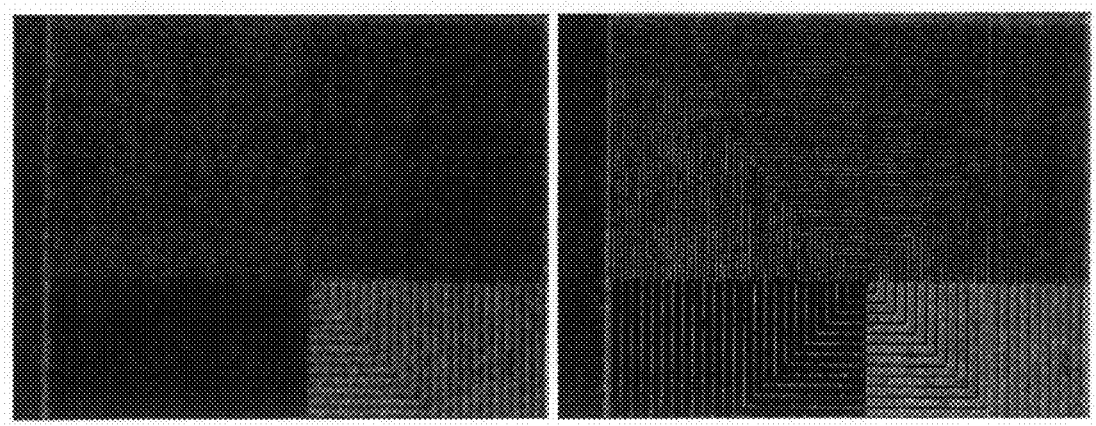
Figure 9D:
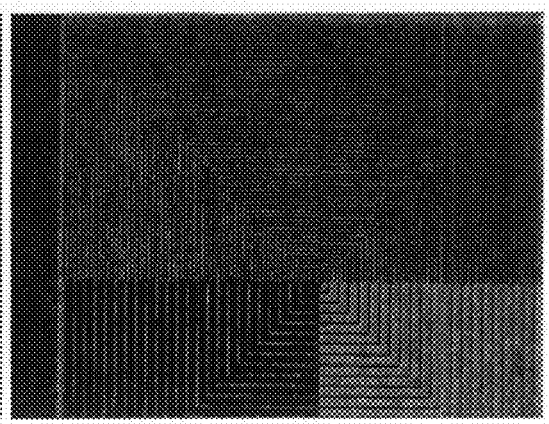
Figure 9E:
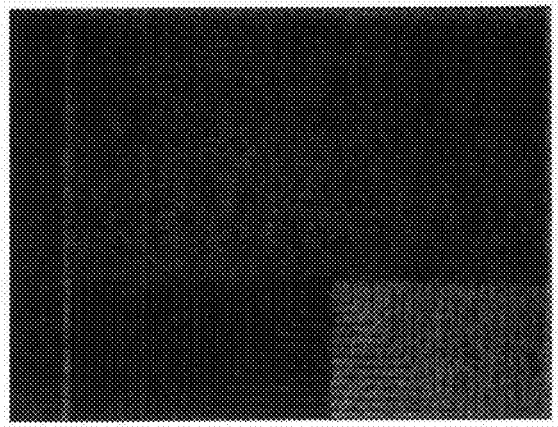
Figure 9F:
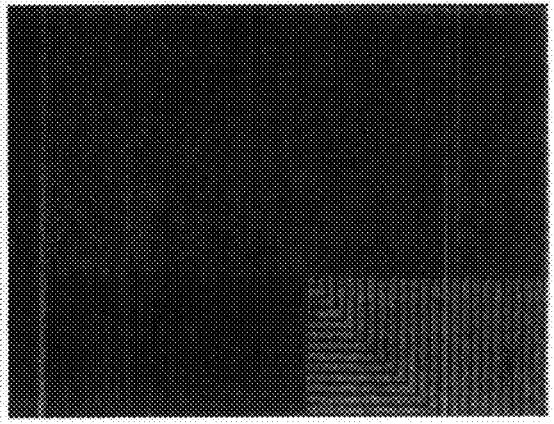
Figure 9G:
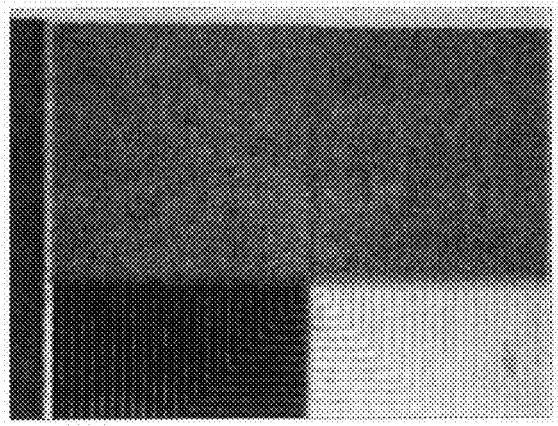
Figure 9H:
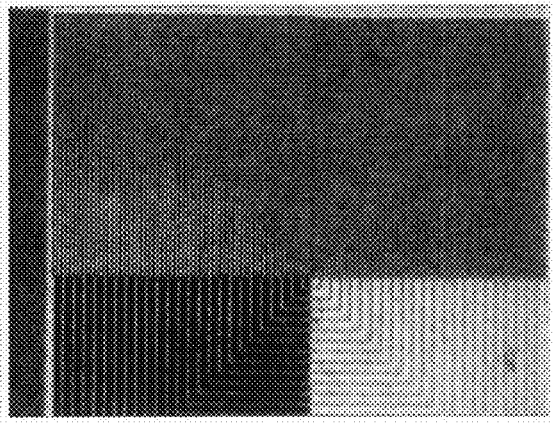

FIG. 9A shows an in focus image obtained without the optical element; FIG. 9B shows the defocused image at $\psi=13$ (+1.5 mm) without the element; FIG. 9C shows the defocused image at $\psi=17$ (+2 mm) without the element; FIGS. 9D-9F correspond to FIGS. 9A-9C but with the optical element; FIG. 9G shows the defocused image at $\psi=13$ (+1.5 mm) obtained without the element with polychromatic illumination; FIG. 9H shows the defocused image at $\psi=13$ (+1.5 mm) obtained with the optical element for polychromatic illumination.

As indicated above, the imaging lens arrangement of the present invention may be used for ophthalmic applications. In order to allow insertion of the imaging lens arrangement into the eye, the surface of the lens arrangement is to be flat. The fabrication techniques suitable to manufacture such an imaging lens arrangement (i.e., flat patterned imaging lens) include for example etching (wet or dry) or laser drilling or lathe grinding to obtain the desired spatial structure (surface relief), and then filling the evacuated volume by a material of a refraction index different from that of the lens, providing a refraction index difference is such that the outer region of the mask is flat while the desired phase difference is generated, required as buffering phase region that generates proper equalization between regions of the lens aperture for the interference effect. Another realization could be by diffusion or photo polymerization that does not include developing or removing of the polymerized material. Yet another approach which is related to eye surgery could be by implanting artificial tissue having difference in refraction index in comparison to the existing tissue of the eye. The EDOF element of the present invention (having no optical power) is added to the focal power of a certain lens which is to be obtained. For example, if a patient needs −1 diopter glasses and 3 diopters glasses for near and far visions, the EDOF element of the present invention may be appropriately designed to be used on either one of these glasses, being configured in accordance with the respective lens aperture to allow a depth of focus region equivalent to 5 diopters. Actually, in this specific example, a 1 diopter glasses with the EDOF element of the present invention can be used, where the EDOF element is operating around the optical power of the lens (1 diopter) and provides the depth of field region from −1.5 to 3.5 diopters. Hence, the patient may use only one pair of glasses with 1 diopter. This focal power of the glasses (imaging lens) will be added to the EDOF element. Such an EDOF element maximizes the defocused OTF of the lens arrangement (appropriately modulates the CTF profile of the imaging lens of the respective glasses) by generating proper phase interference relation between light portions passing through different regions of the lens, to reduce a quadratic phase factor resulting from light getting out of focus of the imaging lens. The inventor has found that for most patients a common EDOF element configuration can be used, preferably as that of FIG. 2C. Turning back to FIG. 2C, the basic period (of the basic element BE) is about 3 mm, a distance between two adjacent bars is about 1.875 mm, and the bar thickness is about 0.375 mm.

If the EDOF element with its range of depth of focus is used on top of a lens in ophthalmic applications, such as a contact lens, then it may be translated into Diopters range. The diameter of the eye lens (effective aperture of the imaging lens) varies from 2 mm up to 6-7 mm depending on the lighting conditions. The optical element generates a Diopter range within which the image is in focus. The inventor has found that for the resulted range of the phase factor ψ (about up to 17) for lightened environment in which the eye pupil has a diameter of 2 mm, the obtained Diopter range P is more than 5 (from −2.5 up to 2.5). The simulations followed the formula:

$$P = \frac{4\Psi\lambda}{\pi D^2} \quad (6)$$

Figure 10A:
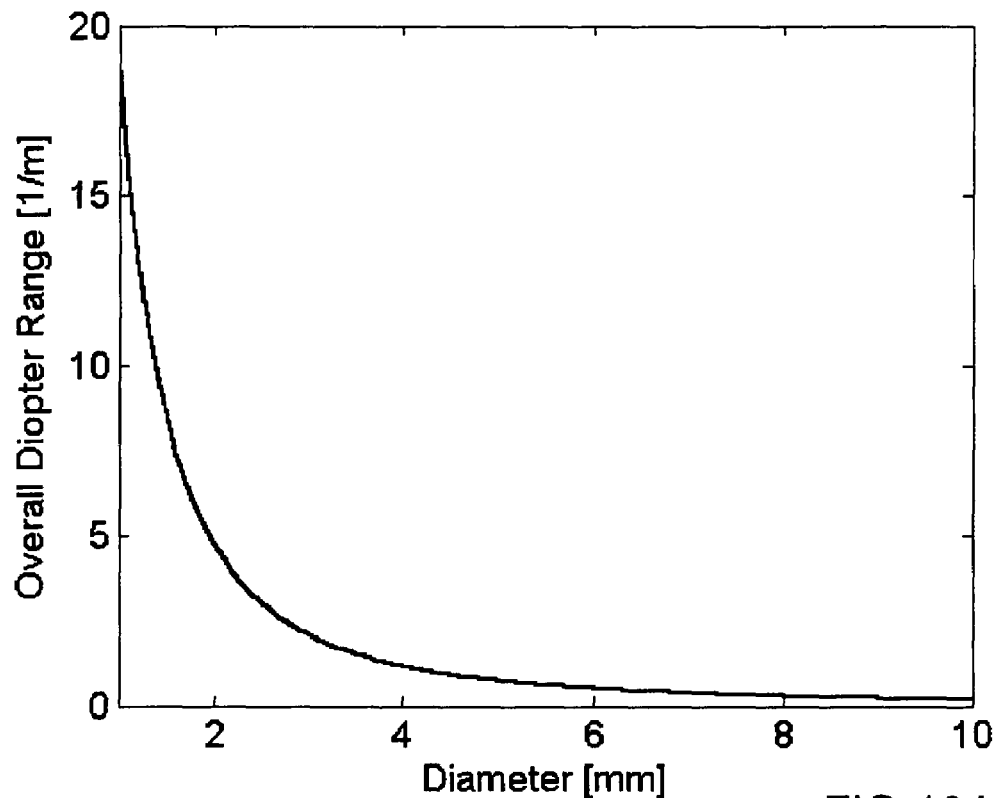
FIG. 10A illustrates the performance of the ophthalmic depth of focus application of the present invention, for the case where the optical element is attached to a contact lens.
Figure 10B:
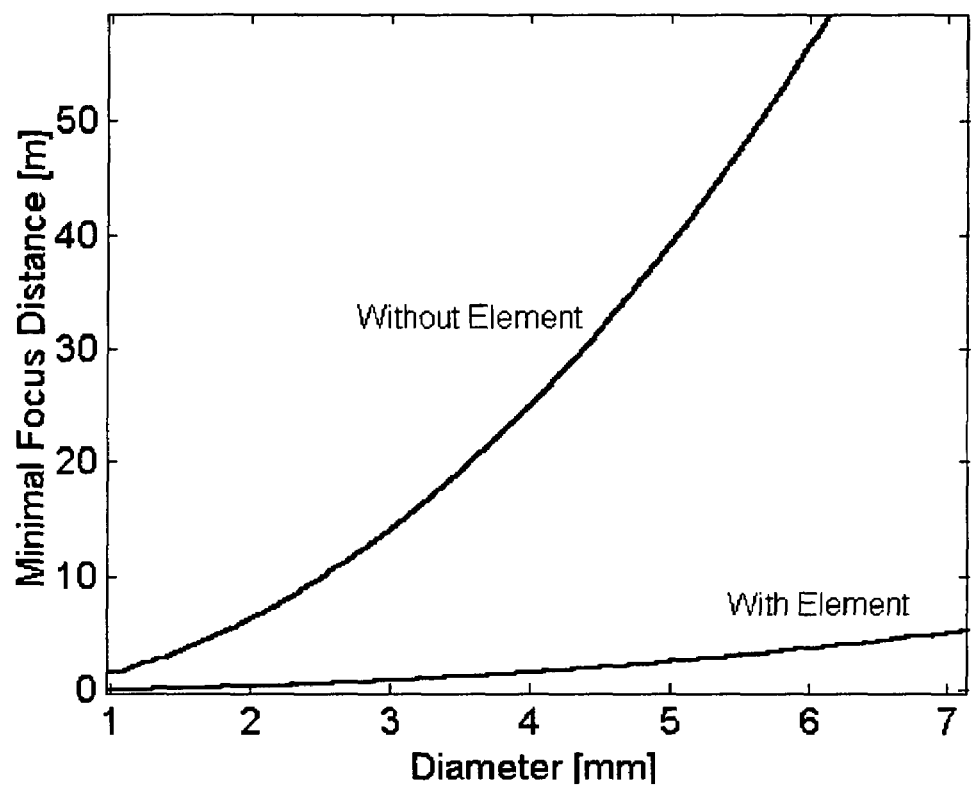
FIG. 10B illustrates the performance of the ophthalmic depth of focus application of the present invention, for the minimal range at which focus is obtained with and without the optical element of the present invention.

FIGS. 10A-10B present the simulation results visualizing the performance of the ophthalmic depth of focus application of the present invention. The simulation of FIG. 10A corresponds to the overall Diopter range obtained due to the fact that the EDOF element is attached to a contact lens. The diameter of the eye lens varies from 2 mm up to 6-7 mm depending on the lighting conditions. The simulations follow Eq. 6 above.

In the simulation of FIG. 10B, an imaging lens with a fixed focal length is used. If the distance between the lens and sensor equals to its focal length (v=F) then the image will be in focus starting from a certain distance, $u_{min}$, up to infinity, wherein the distance $u_{min}$ is determined as:

$$u_{min} = \frac{1}{\frac{4\lambda\Psi}{\pi D^2} + \frac{1}{F} - \frac{1}{v}} = \frac{\pi D^2}{4\lambda\Psi} \quad (7)$$

and for v=F one obtains:

$$u_{min} = \frac{\pi D^2}{4\lambda\Psi} \quad (8)$$

The chart for $u_{min}$ with and without the EDOF element of the present invention is plotted in FIG. 10B. As could be seen, the minimal distance is much smaller when the invented element is in use. Thus, the overall range of focus is much larger. It should be noted that for the human eye, v=15 mm.

Turning back to FIG. 1C exemplifying an imaging arrangement of the present invention formed by a lenslet array and an EDOF elements' array (suitable to be used with a display panel or screen), the required parameters of the imaging arrangement can be estimated as follows:

Let us assume that u, which is the distance between the screen 13 and the lenslet array 12A is about 2 mm; v, which is the distance between the screen 13 and the closest focus plane FP is 40 cm; and R, which is the distance between the eye 16 and the closest focus plane FP, is about 1 m. The object 13 is constituted by the display of the mobile phone or the screen. Basically, the lenslet array 12A images the object plane 13 on the closest focus plane FP, i.e.:

$$\frac{1}{u} - \frac{1}{v} = \frac{1}{f}$$

$$f = \frac{uv}{v - u}$$

which provides f=2.01 mm.

The defocusing parameter is defined as:

$$\Psi = \frac{\pi D^2}{4\lambda} \left| \frac{1}{u} - \frac{1}{v} - \frac{1}{f} \right|$$

where λ is the wavelength.

With the use of EDOF, this parameter can reach the value of 15 and without the EDOF element—the value of 2-3 without distorting the image quality. The diameter, D, of the lenses in the lenslet array can be found such that the minimal value for the distance between the screen 13 and the closest focus plane FP, ($v_{min}$), will be very close to the object plane 13 to have minimal demagnification. The demagnification factor is:

$$M_T = \frac{v_{min}}{u}$$

To have $v_{min}$=u=2 mm, one needs:

$$D = \sqrt{\frac{\Psi \lambda f}{\pi}}$$

This yields:

$$D = \sqrt{\frac{15 \cdot 0.5 \ \mu m \cdot 2.01 \ mm}{\pi}} = 70 \ \mu m$$

It should be noted that without the EDOF element the minimal distance v would have been:

$$v_{min} = \frac{1}{\frac{1}{u} - \frac{1}{f} - \frac{\Psi_{max}\lambda}{\pi D^2}}$$

$$= \frac{1}{\frac{1}{2 \ mm} - \frac{1}{2.01 \ mm} - \frac{2 \cdot 0.5 \ \mu m}{\pi \cdot (70 \ \mu m)^2}}$$

$$= 16 \ mm$$

which means a demagnification factor of 8 (16 mm/2 mm). Such a demagnification would not have allowed seeing the characters in the display.

Attachment of the lenslet array 12A to the screen decreased the visible resolution. The resolution of such an imaging system is limited by the factor of:

$$\delta x = 1.22 \cdot \lambda \frac{f}{D} = 1.22 \cdot 0.5 \text{ μm} \frac{2.01 \text{ mm}}{70 \text{ μm}} = 17.5 \text{ mm}$$

Since the details appearing in the screen are larger than that, the resolution is not damaged by the imaging lenslet array.

Following the computations presented above, a person with normal vision that will focus his eyes on the screen (or on a plane positioned 2 mm behind it) will see the image in focus as well.

The technique of the present invention could be barrier breaking in a vast set of applications including, but not limited to, the following: conventional office devices containing camera such as camcorders, scanners (e.g., barcode scanners) and web cams; conventional imaging systems including camera and detectors, i.e. cellular cameras, car cameras, surveillances cameras, machine vision, photography, HDTV, video conferences, radar imaging systems (that typically suffer from defocus problems), endoscopy and passive bio medical inspections, tomography, display panels, etc. The usage of the depth of focus extending element of the present invention in endoscopy and passive biomedical inspections allows for in-body imaging to see organs in focus that otherwise are not, since there is no control on the exact position of the medical apparatus. Some other possible applications of the present invention include correcting chromatic aberrations in various optical systems, for example in optical communication; media reader/writers used with information carriers such as conventional DVD, or multi-layer information carriers utilizing light reflection or fluorescence.

The present invention may also be used in ophthalmic applications as a contact lens, a spectacle lens, an intraocular lens, or any other lens used around or inserted into any part of the eye. An obvious example is the use of the invention for the benefit of short sighted (myopic) people who develop presbyopia, the need for reading glasses as a result of age-related changes in their natural eye lens. In such an application, those people may use a single lens, as a spectacle lens, contact lens, intracorneal lens, phakic intraocular lens or aphakic intraocular lens, or a lens inserted elsewhere in the eye. In this fashion, they will use one lens for seeing at any distance, near or far. Another obvious utilization of the invention is in an intraocular lens, the artificial lens implanted in the eye after removal of a cataract. Currently, the regular artificial lens has only a single focus and thus the person into whose eye the lens was implanted has a very limited depth of focus and has to use spectacles for most distances of regard. Incorporation of the invention into the implanted lens will afford the patient focused vision at all distances. Another example of ophthalmic use is as a replacement of multifocal (progressive) spectacle lenses, which are conventionally designed such that every segment of the lens surface has a different focus and thus the patient has to move his eyes to focus on objects at different distances. Incorporation of the invention into a spectacle or contact lens will enable the presbyopic wearer to see objects in focus at all distances through any part of the lens.

In all the applications of the invention, including the examples above, the image from objects at different distances are focused on the retina (or sensor) without appreciable loss of energy, in contradistinction to the situation in multifocal contact or intraocular lenses.

Considering the ophthalmic applications of the invention, it should be noted that the technique of the invention, when used specifically in such applications, advantageously enables widening the field of focus and allows clear vision for far distance as well as for near distance and for the range in between.

The presently existing products for the ophthalmic applications include glasses, contact lenses, and intraocular lenses (IOLs). The problems needed to be solved are in the following. In normal, healthy eyes, each eye has two refractive areas (lenses). The difference between the lenses is that dioptric strength of one lens is, within short times, constant and its shape does not change. This lens is the cornea. The second lens that is situated behind the iris is called the "crystal lens" and it is flexible—its dioptric strength is changed by the use of muscles. When the eye lens is relaxed, its bent radius is large and its dioptric power is relatively small (about 15-16 diopters), which enables a person to see far-away objects in focus. When a person wants to see close objects, the dioptric strength of the lens needs to be increased (because otherwise the picture would be formed behind the retina). The increase in dioptric strength is obtained by contracting the lens; in the process called "accommodation". For a person wanting to refocus from far to close (up to 30 cm) distances, the lens has to accommodate by 3 diopters. The ability to add such dioptric strength will enable a person to see in focus from various distances. Usually, around the age of 40, the flexible lens begins to harden, and the eye muscles become less effective, so that it becomes difficult to see close objects. This phenomenon is called "presbyopia". Many of the presbyopic people also have a reduced far-vision (myopia or hyperopia). In these and some other cases there arises a need for correcting the focusing ability for various distances simultaneously.

Another known problem is astigmatism—the phenomenon associated with variation of the eye's optical power with change in the direction of optical axis. For example one eye may require a correction of one diopter along one axis, while a different correction or no correction for another optical axis. The astigmatism typically is due to asymmetry of the cornea or tilting of the crystal lens. When an eye requires two different corrections along two axes with an angle between them being 90 degrees, this is called "regular astigmatism". When the angle is not 90 degrees, this is called "irregular astigmatism". Today, there are some techniques for correction of regular astigmatism. As for the irregular astigmatism, generally it can be corrected by using a hard contact lens creating new surface for the eye. However, many (even most) people having irregular astigmatism have also a cornea condition that does not allow wearing such hard contact lens. The technique of the invention offers a novel solution for the problem of both regular and irregular astigmatism.

For correction of presbyopia, particularly for correction of far vision (related to myopia/hyperopia) there exist two typical spectacle-based correction techniques, which though are based on the same idea: the lens is divided into various fields with different focal distances.

In particular, the spectacle can utilize bifocal glasses, i.e. glasses for focusing at two different distances. The top half of the lens can enable a person to see objects from far and the lower half can enable him to see objects close up (it is usually used for reading and seeing objects at a distance of 40 cm). Bifocal glasses though may have unaesthetic appearance, with a line separating the two halves of each lens, and also they do not help focusing on middle distance objects, such as TV or computer screen.

The spectacle can also utilize multifocal glasses—two parts of which lenses are still for far focus (top portion) and for close up (the lower portion). Between them there is a narrow strip where the top portion changes slowly to the lower portion. A person can thus see from various distances from 40 cm to far away, but only at one object at a time, not close and far at once. The narrow strip is for seeing middle distance objects—so the person has to be 'skilled' to wear such glasses. While seeing through the narrow strip, person may not turn his eyeball, but rather has to move his/her head and follow the middle distance object to continue seeing it in sharp focus. Typically, in these glasses, the visual field is less than 30 degrees for the reading area, and less than 15 degrees for seeing middle distance objects. Thus, in some cases it may take time for a person to get accustomed to wearing the multifocal spectacles, and in some cases the person never gets used to them. Moreover, manufacturing such glasses is relatively costly.

Correction can also be done with contact lenses. For example, on the periphery of the lens there may be made a ring with a focal distance for a near field of vision: typically, close up vision is needed for reading, and when reading the eyes usually need to look downwards, thus the lens will be pushed upwards, and the pupil will use the optical access through the ring. Though, such a solution is not helpful for seeing middle distance objects like a computer screen.

Presbyopia or myopia correction thus can be based on use of bifocal or multifocal contact lenses, made for example with diffractive or refractive rings. However in this case double images are typically seen. Also the energetic efficiency is damaged and people have worse vision at low lighting conditions (e.g. they may not read at such lighting conditions). Yet another technique is to correct one eye for distant objects, and the other eye for close up objects. This solution results in poorer quality, if compared to the case when both eyes see the same objects with the same degree of quality. For example this solution reduces the stereoscopic vision ability.

Turning to IOL lenses, two types of them exist. In the first type, the lens is inserted between the cornea and the iris and it aims at changing the focal distance of the cornea, while not relying on multifocality. Artisan and Artiflex are examples of products implementing such lenses. They are implanted into eyes of those people whose lenses are normal but require refraction correction of the eye. This is the procedure used in laser eye operations known today.

IOL lenses of the other type are inserted in place of the eye lenses. This procedure is performed when a person's eye lens is removed, e.g. due to cataract. Three most important multifocal types of such IOLs exist today: diffractive lenses, refractive lenses, and accommodative lenses.

The diffractive lenses have two different focal points, whereby one of these points is for close up and the other is for far distance. Such lenses, first, distribute the light energy between the focal points; second enable only partial focusing on middle distance objects, between the two focusing lenses; third are typically sensitive to wavelengths (when and because the lens rings are diffractive). Therefore the person may see a picture where some colors are in focus while other colors are out of focus. The refractive IOLs also distribute energy between foci and may provide inadequate quality of middle distance vision.

Accommodative lenses are those imitating the natural eye lens: they can move or can change the length of focus when the eye muscles put pressure on it. Such lenses require a complicated insertion procedure and their technology is yet immature.

Turning now to astigmatism, the regular astigmatism can be corrected by glasses or contact lenses. For making glasses, the angle of astigmatism has to be determined by an accurate testing. The lens needs to be manufactured with high precision. For making use of contact lenses, they need to remain stable in the eye. Thus a contact lens is used with a small weight (stabilizer) preventing it from moving around the pupil. Such contact lenses are custom-made according to the angle of astigmatism, and are costly.

The IOL lenses do not presently provide an accepted solution for astigmatism. Even to the contrary, the IOL insertion procedure may lead to creation of various astigmatic problems. For example, the astigmatism may be worsened if a surgeon would orient the lens at an angle different from the angle of astigmatism or the aperture through which the lens is inserted would cause curvature of the cornea. Hence, nowadays it is common practice that a person with even an astigmatism of one diopter is not advised to have a IOL multifocal lens implant.

Turning now to the technique of the present invention, it is suitable for application with glasses, contact lenses and intraocular lenses. It can be applied to stretch and broaden the depth of focus for a single-, bi- or multifocal lens. The technique does not need to rely on a certain angle or on eye's ability to focus, and so it can be applied for correction of presbyopia, myopia and regular as well as irregular astigmatism.

In particular the technique of the invention can stretch the depth of focus for example making it 3 diopters for pupil size varying between diameters of 1.5 mm up to 5 mm.

For the use with contact lenses and IOLs, the phase element positioned close to the lens or IOL principal plane (or two phase elements at opposite sides of the lens principal plane) may be sufficient to correct simultaneously all the vision problems mentioned above. The phase element may be produced as a surface to which a patterned coating of a similar refractive index is added. Such fabrication procedure is generally less costly than bifocal or multifocal lens fabrication procedure.

It should be noted that the technique of the present invention allows for using the phase affecting element in the following positions in the eye: (1) being attached or incorporated in the eye lens (crystal lens); being located in the anterior chamber (aqueous humour) between the iris and cornea; or being located inside the cornea. In the latter case, the upper, external layer of the cornea is first removed, the phase element is placed (forming a thin layer of about 10 microns), and the removed layer is returned back.

For the use with glasses, the phase element may be reproduced on the surface of the glasses lens, e.g. it may include periodically or non-periodically replicated phase-transition pattern. With regards to the non-periodic replication, the replication may be made for example with slowly changing period (frequency), so as to generate, by the glasses, a consistent focal point. For example, addition of the element can enable the person to see things close-up with the same glasses used for far vision. A large, even an entire field of view may be corrected for both far and near vision. It should be noted that the phase affecting element may advantageously be used in sun glasses as well, where the sun glasses either have certain optical power or not.

As indicated above, the lenses can be produced with phase elements on both sides. This facilitates obtaining uniformly high quality of vision within the large or full field of view. In some embodiments, using a phase element including many phase transitions (e.g. replicated phase pattern), the vision quality may be improved if the phase effect of the phase transition is varying. If the phase pattern is realized as a plurality of binary phase transitions, the phase transitions may be of different height.

The phase element of the invention is not required to have any focal power if used with a lens (though in some embodiments it is integral with the lens and therefore not separable). Though, it allows well focused and highly resolved all-optical imaging. In digital camera imaging post processing of obtained image might be performed, but this is not the case of ophthalmic applications.

As it has been mentioned above, the phase affecting element of the invention is non-diffractive (has relatively large features and relatively low spatial frequencies of the features distribution) and configured to have a reduced sensitivity to quadratic phase factor, affecting the OTF more when the image is defocused and/or at relatively high spatial frequencies. The quadratic phase factor is relevant only for spatially incoherent light: it as a result of the auto correlation operation applied to the phase distribution in the aperture plane (as in (4)). Since all typical conditions involve illumination with incoherent light, the operation of the element of the invention suits the ophthalmic applications.

The auto correlation (4) of the spatial phase distribution over the aperture plane can be written as:

$$H(\mu_x, \mu_y; Z_i) = \frac{\int_{-\infty}^{\infty}\int_{-\infty}^{\infty} P\left(x + \frac{\lambda Z_i \mu_x}{2}, y + \frac{\lambda Z_i \mu_y}{2}\right) P^*\left(x - \frac{\lambda Z_i \mu_x}{2}, y - \frac{\lambda Z_i \mu_y}{2}\right) dx\, dy}{\int_{-\infty}^{\infty}\int_{-\infty}^{\infty} |P(x,y)|^2 dx\, dy} \quad (9)$$

While in focus, P(x,y) is the binary pupil function, which is "1" within the pupil, and "0" outside, $\mu_x, \mu_x$ are the spatial frequencies, $Z_i$ is the distance between the imaging lens and the sensor (retina) and x, y are the spatial coordinates in the aperture plane.

When the phase element of the invention is included in the optical system and defocusing is introduced, the generalized pupil function can be described as:

$$P(x,y) = |P(x,y)| \exp[ikW(x,y)] \quad (10)$$

Here W(x,y) is a quantity proportional to the phase of the wave distortion; and wave vector k equals $2\pi/\lambda$.

If the distortion is caused only by defocusing, W(x,y) has the form of:

$$W(x, y) = W_m \frac{(x^2 + y^2)}{b^2}, \quad (11)$$

where b is the radius of the aperture P (similarly to (1)); the coefficient $W_m$ determines the severity of the defocusing (the deviation from the geometric focusing condition, similarly to (2)).

One of the aspects of the invention is to design a phase only element having large spatial features such that the auto correlation operation of (10) will generate OTF that is invariant over the desired field of view to quadratic phase distortion created when defocusing, as in (2), is introduced. This condition can be defined mathematically through various criteria, generally requiring the OTF to be as much as possible away from zero for a certain region of focus in certain region of spatial frequencies.

For ophthalmic applications several additional factors need to be considered. For example the spectacles are typically about 1.5-2 cm (or more than that) away from the aperture plane of the lens of the eye. A person needs to change his/her line of sight. The diameter of the eye pupil of a person depends on illumination conditions and varies in the range 2-4 mm. In preferred case, the spectacles and contact lenses do not require very precise positioning or orienting.

Hence, the spectacles need to generate the effect of the phase element for a wide field of view and not for a certain line of sight. This is also true for contact lenses and IOLs, but these can move more or less together with the eye ball and its varying line of sight, so the condition may be relaxed.

The inventors have found that the above ophthalmic-related goals can be at least partially fulfilled by spatial replicating of a basic phase pattern structure. For example, a better performance has been achieved with a periodic phase pattern structure on both sides of the glass of the spectacles.

The inventors have conducted experiments proving the applicability of the technique of the invention in the ophthalmology. In particular, the inventors have fabricated a phase element (and an experimental optical system) that provided extended depth of focus within 3 Diopters, for eye pupil diameter varying in the range of 2-4 mm and with high tolerance to the exact position of the element relative to the pupil of the eye lens. Thus, several embodiments provided correction for presbyopia, since the 3 Diopters improvement significantly improved the quality of near vision while substantially not affecting the high quality of far vision. It should be understood, that the obtained 3 Diopters range of improvement is similar to accommodation in that the element itself does not distribute energy between foci and is generally non-diffractive. In fact, when the phase element is positioned in front of the eye it provides the depth of focus within the range of 0-3 Diopters. If the element is added to a lens of for example 2 Diopters optical power, the operation range is 2-5 Diopters.

Figures 11A, 11B:
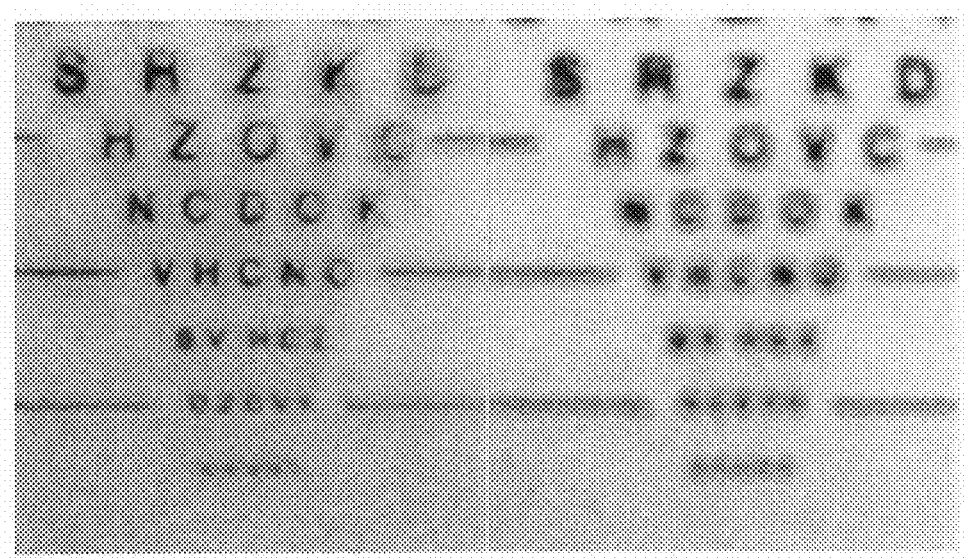
FIGS. 11A and 11B present two images of a typical visual acuity resolution target, respectively, obtained by the technique of the invention and by an optical system with presbyopia with 1.75 Diopters.

FIGS. 11A and 11B present two images of a typical visual acuity resolution target, respectively, obtained by the technique of the invention and by an optical system with presbyopia with 1.75 Diopters. The imaging optical system was built with optical parameters equal to those of the human eye, in accordance with the publication L. A. Carvalho, "A simple mathematical model for simulation of the human optical system based on in vivo corneal data," Revista Brasileira de Engenharia Biomedica, 19, 29-37 (2003). One may see that indeed improvement of 1.75 Diopters is significant (each line in the resolution target is equivalent to 0.25 Diopters). The pupil diameter used in this experiment was 2.5 mm while the phase element was positioned 17 mm away from the pupil.

Here are some definitions of the parameters used to test and quantify the ophthalmic performance. Visual acuity (VA) is defined as the resolving power of the eyes' optical system, or the ability to see two separate objects as separated. Snellen acuity chart includes letters that are constructed so that the width of a stroke equals the width of a gap. In most Snellen charts, letters are 5 units high and 4 units wide. Visual acuity is specified in terms of the angular size of the gap for the smallest sized letter the patient can identify. "Normal" VA is specified as the ability to detect a gap subtending 1 minute of arc. For any target distance, the linear width of the gap $\chi$, for any given angular sub tense, may be determined as follows:

$$\tan\theta = \frac{x}{R},$$

where R is the distance to the target in meters. For a gap subtending 1 minute of arc, and distance of R=6 m one obtains:

χ=6 m·tan θ=6 m·0.000291=0.001746 m=1.746 mm

For the Snellen fraction (SF) the definition is:

$$SF = \frac{R_T}{R_S},$$

where $R_T$ is the testing distance and $R_S$ is the distance at which the smallest letter read subtends at angle of 5' of arc.

The 6/6 acuity standard can be described as a minimum angle of resolution (MAR) of 1 min arc. Log MAR is the logarithm at base 10 of the MAR in min arc at a viewing distance of 6 m. In this system each step is 0.1 log units. The 0.1 'credit' for reading full row of 5 letters can be subdivided into 5×0.02 steps for reading each individual letter.

The contrast sensitivity (CS) is defined as:

$$C = \frac{L_{max} - L_{min}}{L_{max} + L_{min}},$$

where C is the contrast. It is computed for sine wave gratings while the spatial frequency is plotted along the x axis and the CS is plotted along the y axis.

Figure 12A:
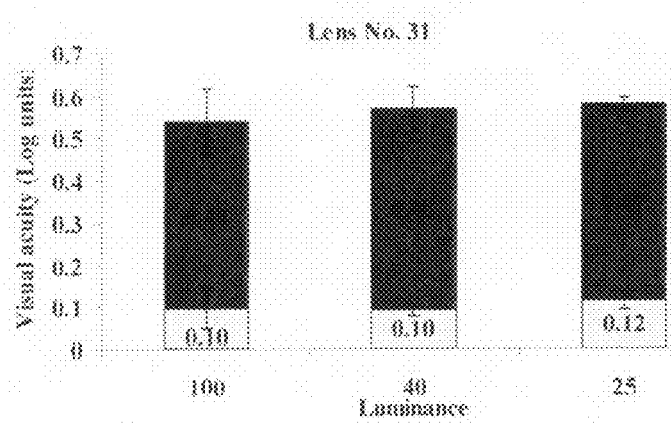
FIGS. 12A-12B and 13 show the ophthalmic experimental results (visual acuity diagrams) obtained using phase elements of the present invention for a group of persons.
Figure 12B:
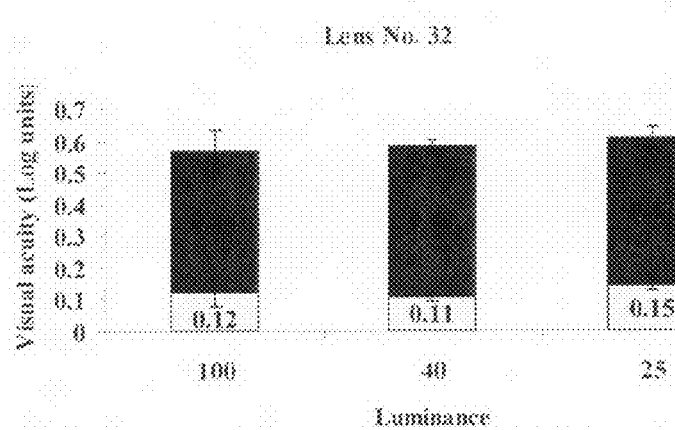

In this way the invention was also tested on a group of persons. FIGS. 12A and 12B present the obtained results (visual acuity diagrams) for two phase elements, numbered 31 and 32. The shown improvement in visual acuity (VA, on the diagrams' vertical axes) relates to the improvement in Diopters (D), resulted from the increased depth of focus due to the phase element:

D=2.5·VA       (12)

Elements 31 and 32 had annular like structure with external diameter of 2.6 mm for the ring replicated with basic period of about 3.5 mm and etched depth of 350 nm (equivalent to generated phase difference of about π/2). The elements were fabricated on both sides of a flat glass of 2 mm width. The number of replicates was either 4 or 5. The difference between elements 31 and 32 was in slight change in the diameter of the basic pattern and in its etching depth.

All of the tested persons were examined by an optometrist and had far VA of 6/6 or better. None of them had deficit in color vision or contrast sensitivity. All of the persons had presbyopia and needed optical correction for near distance. VA tests were made with logarithmic charts, Precision Vision chart for testing at 40 cm and Early Treatment Diabetic Retinopathy Study (ETDRS) for testing at distance. The group included 5 persons at age range from 49 to 65 with an average of 55±3.4. The persons were tested at three different luminance conditions (100, 40, and 25 Watts of the illuminating lamp) which affected the pupil size: the high luminance led to the pupil sizes of 1.5 to 2.5 mm, the medium luminance to the pupil sizes of 2.5 to 3.5 mm, and the low luminance to the pupil size of 3 to 4 mm.

It can be seen from FIGS. 12A and 12B that the achieved improvement in VA was substantial for the three luminance conditions.

For example, the phase element 31 has improved the near distance VA for the high, middle and low luminance to 0.096±0.048, 0.95±0.014 and 0.115±0.048 in Log units respectively (these visual acuities are shown as lower and lighter portions of the vertical bars). The improvement in the visual acuity is the difference between the upper (darker) portions of the bars and the lower (lighter) portions of the bars, e.g. 0.34 (0.44–0.1) for element 31 at illumination power of 100 W. In both FIGS. 12A and 12B the standard deviation is designated as a line plotted on top of the bar presented for each measurement.

The persons of the test group were asked to read. Table 1 presents the results obtained with invented elements 51 and 52 All the tests were taken with the high luminance only.

TABLE 1

Summary of the reading test.

| VA with distance correction (ETDRS Log units Jaeger and Snelen) | VA with distance correction and EDOF lens | Improvement | EDOF element No | Refraction | ge |
|---|---|---|---|---|---|
| 0.6 J8 6/24 | 0.1 J1 6/7.5 | 0.5 | 52 & 51 | Myopic −5.00 − 1.25 × 76 | 56 |
| 0.62 J8− 6/24− | 0.2 J4 6/9.5 | 0.42 | 52 & 51 | Myopic −2.75 | 53 |
| 0.54 J6− 6/19− | 0.12 J1 6/7.5 | 0.42 | 51 | Myopic −0.5 − 100 × 80 | 65 |
| 0.54 J6− 6/19− | 0.12 J1 6/7.5 | 0.42 | 51 | Hyperopic Plan | 52 |

Elements 31, 32, 33, and 35 were tested for far distance vision as well: the results of the distance vision tests are summarized in Table 2. The results show small deficit, less than 0.1 Log units, in VA for most of the persons. Different rows correspond to different persons.

TABLE 2

Summary of the effect of the invented element on far vision.

| Element No. 35 | Element No. 33 | Element No. 32 | Element No. 31 | Corrected Visual Acuity for Distance |
|---|---|---|---|---|
| −0.06 | −0.1 | −0.1 | 0.08 | −0.08 |
| 0.22 | 0.2 | 0.16 | 0.26 | 0 |
| 0.08 | 0.18 | −0.12 | 0.26 | −0.06 |
| 0 | 0.06 | 0.04 | 0.24 | 0.06 |
| −0.02 | −0.02 | 0.04 | −0.02 | 0.04 |
| 0.44 | 0.064 | 0.004 | 0.164 | −0.008 |
| 0.055 | −0.064 | 0.057 | 0.06 | 0.03 |

Additional tests that were performed over the test group included:
- 5 persons were tested monocularly with the "Ichihara" color test, no reduce in performance was found for any of them. Therefore the element preserves color integrity;
- Contrast sensitivity test with Sine Wave Contrast Test (SWCT) of Stereo Optical Co. Inc. was taken with 5 persons, all showed no reduce in performance or reduce corresponding to their results for the near vision optical correction;

Three dimensional capabilities and stereoscopy were tested. No reduction in stereoscopic capabilities was observed.

It should be understood that the presented approach, although its performance was quantified only for near and far vision, produces axially continuous focused vision (i.e. continuously extended depth of focus).

Figure 13:
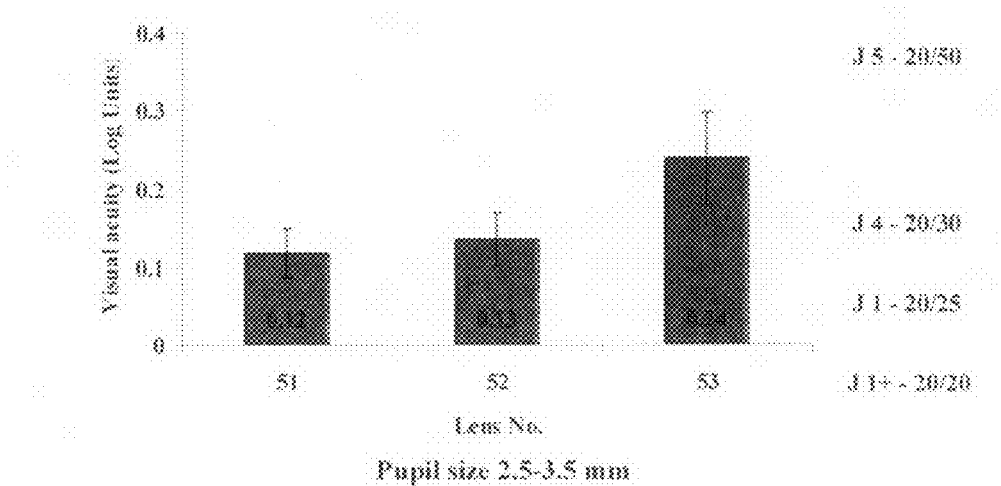

FIG. 13 presents similar results (the improvement in the visual acuity) obtained for elements 51, 52 and 53 when tested with the same test group. The results in Jaeger units appear in the right part of the plot. This group of elements is similar to elements 31, 32, 33, 35: the difference is in the size of phase pattern period and the etching depth (the variation was few percentages in comparison to the values previously specified for elements 31, 32, 33 and 35).

As it has been mentioned above, a large portion of population, especially of the bifocal population, has regular or even irregular astigmatism which means that their eye has different focal lengths along different spatial axes. The technique of the present invention uses the phase element providing an extended depth of focus for achieving high imaging quality for both cases of astigmatism. The presented solution was experimentally tested with an optical setup modeling the human eye.

To this end, the invented annular phase element has been used with large spatial features configured for being relatively insensitive to quadratic phase of defocusing under the condition of spatially incoherent illumination. The element can be used with spectacles as well as with contact lenses or IOLs.

The optical element was positioned 17 mm away from the imaging lens that modeled the human eye. Astigmatism was inserted into that lens (either regular or irregular. The phase element was an annular like structure with external diameter of 2.6 mm for the ring (as described above), replicated with basic period of about 3.5 mm. The etching depth was of about 350 nm and provided a phase difference of about $\pi/2$ for those optical paths passing through the pattern compared to the optical paths not passing through the pattern. The phase pattern was fabricated on both sides of flat glass having width of 2 mm. The fabrication on both sides provided some improvement in performance. Some other elements had the phase transition of other values, such as $\pi$, $1.5\pi$. Generally, the values of the phase effects differ by not more than $16\pi$, $8\pi$, $4\pi$, $2\pi$, dependent on embodiment. Likewise, a lower bound for an average width of the phase transition can be set for example to $5\lambda$, $25\lambda$, $150\lambda$, or $250\lambda$. The larger this characteristic width, the higher the energetic efficiency and the lesser chromatic aberration of the phase-affecting element.

Figures 14A, 14B:
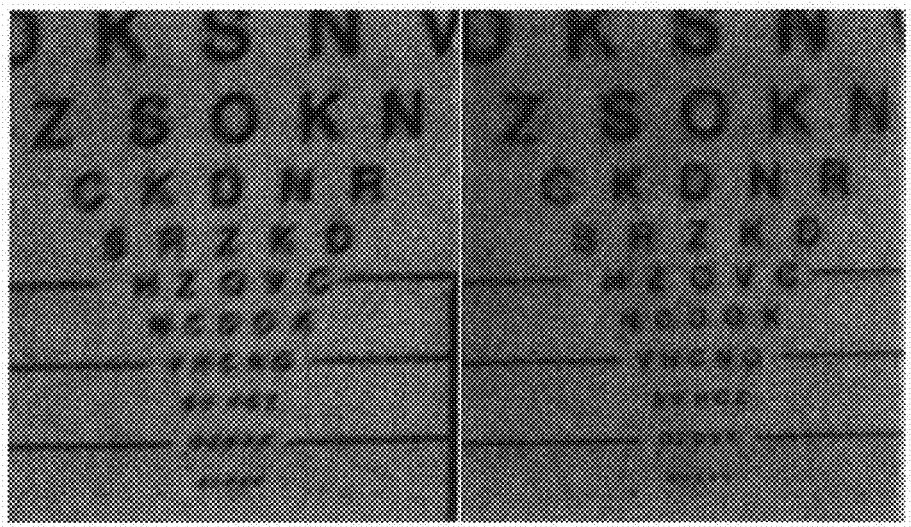
FIGS. 14A and 14B present the ophthalmic experimental results for the technique of the present invention showing improvement of irregular astigmatism.
Figures 15A, 15B:
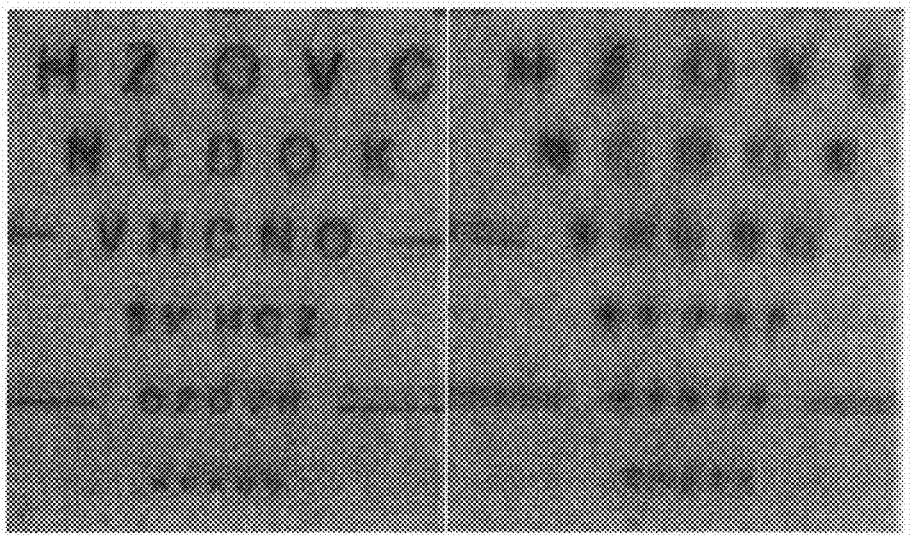
FIGS. 15A and 15B present the ophthalmic experimental results for the technique of the present invention showing improvement of regular astigmatism.

FIGS. 14A and 14B present the obtained experimental results for irregular astigmatism. FIG. 14A is obtained with the phase element and FIG. 14B is obtained without it. Likewise, FIGS. 15A and 15B present the obtained experimental results for regular astigmatism: FIG. 15A was obtained with the phase element and FIG. 15B was captured without it. In both cases of regular and irregular astigmatism one may see a significant improvement that was obtained. This improvement can be estimated to be equivalent to 1.5-2 Diopters (each line of improvement in the ophthalmic resolution chart is 0.25 Diopters).

The technique of the invention can also be used for treatment of myopian people, especially for children. Using glasses is not recommended for myopian children, because it may cause progressing (worsening) of their myopia. With the extended depth of focus treatment eyes do not need to accommodate (since the element extends the focus rather than refocuses the eye), therefore the progress of the myopia can be stopped or delayed. It should be noted that the phase elements may include a combination of local phase patterns arranged in a spaced-apart relationship along two axes, though distributed with a certain degree of randomality. For example similar patterns replicated at various relatively random positions may also be used. Generally, the phase-affecting element may include various geometrical shapes.

Also, as mentioned above the phase affecting element may be formed by non-periodic pattern replication. In this connection, the following should be noted: randomizing the positions of the replicates may provide on average to have more uniform performance over the large field of view. This can be obtained since the replicates are non uniformly spread along the field of view and thus on average for each angle there is a probability of obtaining proper pattern of the phase transitions. In periodic replications, there can be certain angles for which no proper phase-transition appears. On average, in some cases, a more functional or more optimized device can be obtained with non-periodic (e.g. the slightly non-periodic, for example with increasing or decreasing period) or random replication. Also, the use of non-periodic replication can ease the brain adaptation to the phase element since fluctuations in quality of vision can be lower. Therefore the adaptation time required by the brain can be shorter for such a structure. Moreover, the fabrication of such an element with randomly located replicates might be simpler, since no tolerances are required regarding the period of replication. A phase element with randomly located replicates might have better performance for varying illumination conditions because the period does not have to be adapted to the pupil size of the eye.

Those skilled in the art will readily appreciate that various modifications and changes can be applied to the embodiments of the invention described hereinbefore without departing from its scope defined in and by the appended claims.

The invention claimed is:

1. An imaging arrangement comprising: an imaging lens assembly including at least one lens having a certain affective aperture, and at least one optical element associated with said at least one lens and configured to provide an extended depth of focus of the imaging arrangement, said optical element being configured as a phase-affecting, non-diffractive optical element defining a spatially low frequency phase transition, said optical element together with its associated lens defining a predetermined pattern formed by spaced-apart optically transparent features of different optical properties, position of at least one phase transition region of the optical element within the lens plane being determined by at least a dimension of said affective aperture.

2. The arrangement of claim 1, wherein said lens assembly includes the single lens associated with the single optical element.

3. The arrangement of claim 1, comprising the lens assembly including an array of lenses, and an array of the optical elements, each optical element being associated with the corresponding one of the lenses.

4. The arrangement of claim 1, wherein said optical element is configured as a phase-only element.

5. The arrangement of claim 4, wherein said optical element is configured as a binary mask.

6. The arrangement of claim 1, wherein said optical element is a configured as a phase and amplitude affecting element.

7. The arrangement of claim 1, wherein the optical element is configured to maximize a defocused optical transfer function (OTF) of the imaging arrangement by providing the out of focus OTF as much as possible away from zero.

8. The arrangement of claim 7, wherein the optical element is configured to produce proper phase interference relation between light portions passing through different regions of the imaging arrangement corresponding to the different features of the pattern to thereby reduce a quadratic phase factor resulting from light getting out of focus of the imaging lens.

9. The arrangement of claim 1, wherein said at least one transition region is configured as a pi-phase transition for a certain wavelength for which the optical element is designed.

10. The arrangement of claim 1, wherein said at least one transition region is configured as about pi/2 phase transition for a certain wavelength range for which the optical element is designed.

11. The arrangement of claim 1, wherein the position of said at least one transition region with respect to the imaging lens is determined by optical power of the imaging lens.

12. The arrangement of claim 7, wherein the position for N transition regions of the optical element within the imaging lens plane maximizing the OTF is determined as:

$$\max_{a_n}\left\{\min\left\{\left[\tilde{D}(v)\sum_{n=1}^{N}a_n rect\left(\frac{v-n\Delta v}{\Delta v}\right)\right]\otimes\left[\tilde{D}(v)\sum_{n=1}^{N}a_n rect\left(\frac{v-n\Delta v}{\Delta v}\right)\right]\right\}\right\}$$

values for $a_n$ providing maximum for minima of an expression for auto correlation of a Coherent Transfer Function (CTF) of the imaging lens, where $a_n$ equals either 1 or −1, $\tilde{D}(v)$ being the CTF of the imaging lens corresponding to out of focus position of an object being imaged and being determined as $$\tilde{D}(v) = \exp\left(\frac{i4\psi v^2}{D^2}\right),$$

wherein D is the affective aperture dimension, v is a coordinate of the affective aperture in the CTF plane, and $\psi$ is a phase factor representing a degree of getting out of focus.

13. The arrangement of claim 1, wherein said at least one transition region has a sub-pattern formed by an array of variable phase transition sub-regions.

14. The arrangement of claim 9, wherein said at least one pi-phase transition region has a sub-pattern formed by an array of variable pi-phase transition sub-regions.

15. The arrangement of claim 1, wherein the optical element is configured as at least one annular transition region.

16. The arrangement of claim 1, wherein the optical element is configured as a grid.

17. The arrangement of claim 1, wherein said optical element is spaced-apart from the imaging lens along an optical axis of the imaging lens.

18. The arrangement of claim 1, wherein said optical element is attached to the imaging lens.

19. The arrangement of claim 1, wherein said optical element is made integral with the imaging lens.

20. The arrangement of claim 1, wherein said optical element is configured as a mask formed by an array of said transition regions arranged in a spaced-apart relationship being spaced by the optically transparent regions of the imaging lens within the imaging lens plane.

21. The arrangement of claim 1, comprising two phase affecting optical elements located in spaced-apart substantially parallel planes at opposite sides, respectively, of said at least one lens.

22. The arrangement of claim 19, wherein said at least one transition region is formed as a surface relief on the imaging lens surface, defining a lens thickness within said at least one region different from that within other regions of the lens.

23. The arrangement of claim 19, wherein said at least one transition region is formed by a material having refractive index different from that of the imaging lens material.

24. The arrangement of claim 19, wherein said optical element is configured as a mask formed by an array of the phase transition regions formed by a material having refractive index different from that of the imaging lens material.

25. The arrangement of claim 7, wherein the optical element is configured to maximize the OTF by reducing high-frequency cancellation at large shifts of a Coherent Transfer Function (CTF) of the imaging lens.

26. The arrangement of claim 7, wherein the optical element is configured to maximize the OTF by reducing sensitivity of the lens arrangement to shifts of a Coherent Transfer Function (CTF) of the imaging lens while getting out of focus.

27. The arrangement of claim 1, wherein the optical element is configured to produce periodic replication of a lateral phase shape of a light field propagating through the imaging lens.

28. The arrangement of claim 1, wherein the optical element is configured in accordance with a free space propagation of the optical element function for a distance between the optical element and the imaging lens plane.

29. The arrangement of claim 1, wherein the optical element is configured to produce non-periodic replication of a lateral phase shape of a light field propagating through the imaging lens.

30. The arrangement of claim 1, wherein the optical element is configured to produce random replication of a lateral phase shape of a light field propagating through the imaging lens.

31. The arrangement of claim 1, for use in patients' spectacles.

32. An optical element for use with an imaging lens in the imaging arrangement of claim 1 for extending depth of focus of imaging, the optical element being configured as a phase-affecting, non-diffractive optical element defining a predetermined pattern of spatially low frequency phase transitions, said pattern being defined by an affective aperture of the given imaging lens.

33. A system for creating an image of an object on a detector plane, the system comprising the imaging lens arrangement of claim 1.

34. The system of claim 32, wherein said object is a screen of a display device to be imaged on the eye retina constituting the detector plane.

35. A display device carrying the imaging arrangement of claim 1.

36. A method for providing a certain extended depth of focus of an imaging system, the method comprising applying an aperture coding to an imaging lens having a certain effective aperture, by applying to the imaging lens at least one phase-affecting non-diffractive optical element configured to define a spatially low frequency phase transition arrangement and thereby provide a predetermined pattern of spaced-apart substantially optically transparent features of different optical properties within the imaging lens plane, thereby producing phase interference relation between light portions passing through different regions of the lens arrangement corresponding to the different features of the pattern so as to reduce a quadratic phase factor resulting from light getting out of focus of the imaging lens and maximize a defocused optical transfer function (OTF) of the imaging lens arrangement.

37. A method for designing the optical element of claim 32, said designing comprising selecting N positions for the phase transitions within the imaging lens effective aperture as those providing maximal contrast of an Optical Transfer Function (OTF) of the imaging system under a set of out of focus locations, thereby providing the out of focus OTF as much as possible away from zero.

38. The method of claim 37, wherein the positions for said N transition regions of the optical element within the imaging lens plane maximizing the OTF are determined as:

$$\max_{a_n}\left\{\min\left\{\left[\tilde{D}(v)\sum_{n=1}^{N}a_n rect\left(\frac{v-n\Delta v}{\Delta v}\right)\right]\otimes\left[\tilde{D}(v)\sum_{n=1}^{N}a_n rect\left(\frac{v-n\Delta v}{\Delta v}\right)\right]\right\}\right\}$$

values for $a_n$ providing maximum for minima of an expression for auto correlation of a Coherent Transfer Function (CTF) of the imaging lens, where $a_n$ equals either 1 or –1, $\tilde{D}(v)$ being the CTF of the imaging lens corresponding to out of focus position of an object being imaged and being determined as $$\tilde{D}(v)=\exp\left(\frac{i4\psi v^2}{D^2}\right),$$

wherein D is the affective aperture dimension, v is a coordinate of the affective aperture in the CTF plane, and, and $\psi$ is a phase factor representing a degree of getting out of focus.

39. The method of claim 37, comprising fabricating a mask formed by an arrangement of the N transitions spaced-apart from each other in accordance with said selected N positions.

40. The method of claim 39, comprising attaching said mask to the surface of the imaging lens aperture.

41. The method of claim 37, comprising patterning the surface of the imaging lens aperture to form a mask of the N transitions spaced-apart from each other in accordance with said selected N positions.

42. The method of claim 40, comprising providing said surface substantially flat to thereby allow insertion of the patterned imaging lens into a patient's eye.

43. The method of claim 37, wherein the designing of the optical element comprises producing a phase interference relation between light portions passing through said N regions and spaces between them to thereby reduce a quadratic phase factor resulting from light getting out of focus of the imaging lens and maximize a defocused optical transfer function (OTF) of an arrangement formed by the imaging lens and the optical element.

44. The method of claim 41, wherein said patterning comprises applying material removal to the lens regions within said N positions, and filling said regions, from which the lens material has been removed, by a material of a refraction index different from that of the lens, so as to provide a refraction index difference such that the outer region of the patterned lens is flat and proper equalization between the different material regions is provided to produce a phase interference relation between light portions passing through different material regions to thereby reduce a quadratic phase factor resulting from light getting out of focus of the imaging lens and maximize a defocused optical transfer function (OTF) of the patterned imaging lens.

45. The method of claim 41, wherein said patterning comprises applying diffusion or photo polymerization to the lens regions within said N positions, so as to provide a refraction index difference between said N regions and spaces between them such that the outer region of the patterned lens is flat and proper equalization between the different material regions is provided to produce a phase interference relation between light portions passing through different material regions to thereby reduce a quadratic phase factor resulting from light getting out of focus of the imaging lens and maximize a defocused optical transfer function (OTF) of the patterned imaging lens.

46. The method of claim 37, comprising implanting in the patient's eye tissue, within said selected N positions, an artificial tissue having a refraction index different from that of the eye tissue.

* * * * *